United States Patent
Buckanovich et al.

(10) Patent No.: US 9,468,632 B2
(45) Date of Patent: Oct. 18, 2016

(54) METHODS AND COMPOSITIONS FOR TARGETING CANCER STEM CELLS

(71) Applicant: The Regents of the University of Michigan, Ann Arbor, MI (US)

(72) Inventors: Ronald Buckanovich, Ann Arbor, MI (US); Scott D. Larsen, South Lyon, MI (US); Kun Yang, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/647,770

(22) PCT Filed: Nov. 26, 2013

(86) PCT No.: PCT/US2013/072055
§ 371 (c)(1),
(2) Date: May 27, 2015

(87) PCT Pub. No.: WO2014/085485
PCT Pub. Date: Jun. 5, 2014

(65) Prior Publication Data
US 2015/0297577 A1   Oct. 22, 2015

Related U.S. Application Data

(60) Provisional application No. 61/730,832, filed on Nov. 28, 2012.

(51) Int. Cl.
*A61K 31/404* (2006.01)
*A61K 31/4439* (2006.01)
*A61K 45/06* (2006.01)
(Continued)

(52) U.S. Cl.
CPC ......... *A61K 31/4439* (2013.01); *A61K 31/136* (2013.01); *A61K 31/337* (2013.01); *A61K 31/404* (2013.01); *A61K 31/4035* (2013.01); *A61K 31/437* (2013.01); *A61K 31/555* (2013.01); *A61K 33/24* (2013.01); *A61K 45/06* (2013.01); *C07D 209/04* (2013.01);
(Continued)

(58) Field of Classification Search
CPC .................................................... A61K 31/404
USPC ................................................... 514/412, 649
See application file for complete search history.

(56) References Cited

U.S. PATENT DOCUMENTS 4,446,321 A * 5/1984 Schmidt ................ B41M 5/136
544/124

FOREIGN PATENT DOCUMENTS

WO    2008137102 A2    11/2008

OTHER PUBLICATIONS

Russo et al, "Identification of 4-(N,N-dipropylamino)benzaldehyde as a potent, reversible inhibitor of mouse and human class 1 aldehyde dehydrogenase," Biochem. Pharmacology, vol. 50(3), pp. 399-406, (1995).*

(Continued)

*Primary Examiner* — Kamal Saeed
*Assistant Examiner* — Janet L Coppins
(74) *Attorney, Agent, or Firm* — Casimir Jones, S.C.; David Casimir; Tanya Arenson

(57) ABSTRACT

The present invention relates to chemical compounds, methods for their discovery, and their therapeutic and research use. In particular, the present invention provides compounds as therapeutic agents against cancer stem cells.

14 Claims, 9 Drawing Sheets

(51) Int. Cl.
  A61K 31/337   (2006.01)
  A61K 31/555   (2006.01)
  A61K 33/24    (2006.01)
  C07D 401/04   (2006.01)
  C07D 471/04   (2006.01)
  C07D 209/04   (2006.01)
  G01N 33/574   (2006.01)
  A61K 31/136   (2006.01)
  A61K 31/4035  (2006.01)
  A61K 31/437   (2006.01)

(52) U.S. Cl.
  CPC ........... *C07D401/04* (2013.01); *C07D 471/04* (2013.01); *G01N 33/574* (2013.01)

(56) References Cited

OTHER PUBLICATIONS

Schafer et al, "Aldehyde dehydrogenase 1A1—a new mediator of resistance to temozolomide in glioblastoma," Neuro-Oncology 14(12), pp. 1452-1464, (2012).*
Kukidome, J. et al., "The mechanism of cell death in human cultured colon adenocarcinoma cell line COLO 201 induced by b-D-N-acetylglucosaminyl p-nitrophenol", The Tohoku Journal of Experimental Medicine,( 2001), vol. 194, pp. 23-34.*
Balmer et al., "Gene expression regulation by retinoic acid." J Lipid Res. Nov. 2002;43(11):1773-808.
Banh et al., "A novel aldehyde dehydrogenase-3 activator leads to adult salivary stem cell enrichment in vivo." Clin Cancer Res. Dec. 1, 2011;17(23):7265-72.
Canuto et al.,"Aldehyde dehydrogenase 3 expression is decreased by clofibrate via PPAR gamma induction in JM2 rat hepatoma cell line." Chem Biol Interact. Feb. 1, 2003;143-144:29-35.
Chen et al., "A restricted cell population propagates glioblastoma growth after chemotherapy." Nature. Aug. 23, 2012;488(7412):522-6.
Corma et al., "Preparation of substituted anilines from nitro compounds by using supported gold catalysts." Nat Protoc. 2006;1(6):2590-5.
Deng et al., "Distinct expression levels and patterns of stem cell marker, aldehyde dehydrogenase isoform 1 (ALDH1), in human epithelial cancers." PLoS One. Apr. 21, 2010;5(4):e10277.
Driessens et al., "Defining the mode of tumour growth by clonal analysis." Nature. Aug. 23, 2012;488(7412):527-30.
Gasparetto et al., "Aldehyde dehydrogenases are regulators of hematopoietic stem cell numbers and B-cell development." Exp Hematol. Apr. 2012;40(4):318-29.
Ginestier et al., "CXCR1 blockade selectively targets human breast cancer stem cells in vitro and in xenografts." J Clin Invest. Feb. 2010;120(2):485-97.
Gupta et al., "Identification of selective inhibitors of cancer stem cells by high-throughput screening." Cell. Aug. 21, 2009;138(4):645-59.
International Search Report PCT/US2013/072055, Mailed on Feb. 27, 2014, 13 pages.
Irving et al., "Influence of disulfiram on the metabolism of the urinary bladder carcinogen N-butyl-N-(4-hydroxybutyl) nitrosamine in the rat" Carcinogenesis. Sep. 1987;8(9):1309-15.
Kast et al., "Suppressing glioblastoma stem cell function by aldehyde dehydrogenase inhibition with chloramphenicol or disulfiram as a new treatment adjunct: an hypothesis." Curr Stem Cell Res Ther. Dec. 2009;4(4):314-7.
Keung et al., "Daidzin: a potent, selective inhibitor of human mitochondrial aldehyde dehydrogenase." Proc Natl Acad Sci U S A. Feb. 15, 1993;90(4):1247-51.
Koppaka et al., "Aldehyde dehydrogenase inhibitors: a comprehensive review of the pharmacology, mechanism of action, substrate specificity, and clinical application." Pharmacol Rev. Jul. 2012;64(3):520-39.
Kryczek et al., "Expression of aldehyde dehydrogenase and CD133 defines ovarian cancer stem cells." Int J Cancer. Jan. 1, 2012;130(1):29-39.
Kukidome et al., "The mechanism of cell death in human cultured colon adenocarcinoma cell line COLO 201 induced by beta-D-N-acetylglucosaminyl-p-nitrophenol." Tohoku J Exp Med. May 2001;194(1):23-34.
Landen et al., "Targeting aldehyde dehydrogenase cancer stem cells in ovarian cancer." Mol Cancer Ther. Dec. 2010;9(12):3186-99.
Levi et al., "Aldehyde dehydrogenase 1a1 is dispensable for stem cell function in the mouse hematopoietic and nervous systems." Blood. Feb. 19, 2009;113(8):1670-80.
Lin et al., "Disulfiram is a DNA demethylating agent and inhibits prostate cancer cell growth." Prostate. Mar. 1, 2011;71 (4):333-43.
Marchitti et al., "Aldehyde dehydrogenase 3B1 (ALDH3B1): immunohistochemical tissue distribution and cellular-specific localization in normal and cancerous human tissues." J Histochem Cytochem. Sep. 2010;58(9):765-83.
Morrison et al., "Disulfiram induces copper-dependent stimulation of reactive oxygen species and activation of the extrinsic apoptotic pathway in melanoma." Melanoma Res. Feb. 2010;20(1):11-20.
Muzio et al., "Aldehyde dehydrogenases and cell proliferation." Free Radic Biol Med. Feb. 15, 2012;52(4):735-46.
Napoli et al., "Enzymes and binding proteins affecting retinoic acid concentrations." J Steroid Biochem Mol Biol. Jun. 1995;53(1-6):497-502.
Prescott et al., "Long-Chain Thiosemicarbazones as Potential Anticancer and Antiviral Agents." J Med Chem. May 1964;7:383-5.
Sabichi et al., "Retinoic acid receptor beta expression and growth inhibition of gynecologic cancer cells by the synthetic retinoid N-(4-hydroxyphenyl) retinamide." J Natl Cancer Inst. Apr. 15, 1998;90(8):597-605.
Saw et al., "Characterization of aldehyde dehydrogenase isozymes in ovarian cancer tissues and sphere cultures." BMC Cancer. Aug. 1, 2010;12:329.
Schepers et al., "Lineage tracing reveals Lgr5+ stem cell activity in mouse intestinal adenomas." Science. Aug. 10, 2012;337(6095):730-5.
Silva et al., "Aldehyde dehydrogenase in combination with CD133 defines angiogenic ovarian cancer stem cells that portend poor patient survival" Cancer Res. Jun. 1, 2011;71(11):3991-4001.
Wei et al., "Mullerian inhibiting substance preferentially inhibits stem/progenitors in human ovarian cancer cell lines compared with chemotherapeutics." Proc Natl Acad Sci U S A. Nov. 2, 2010;107(44):18874-9.
Yip et al., "Disulfiram modulated ROS-MAPK and NFκB pathways and targeted breast cancer cells with cancer stem cell-like properties." Br J Cancer. May 10, 2011;104(10):1564-74.

* cited by examiner

Figure 2
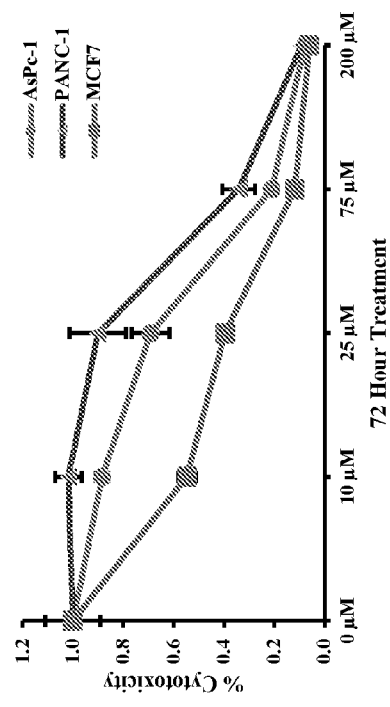
Fig. 2A
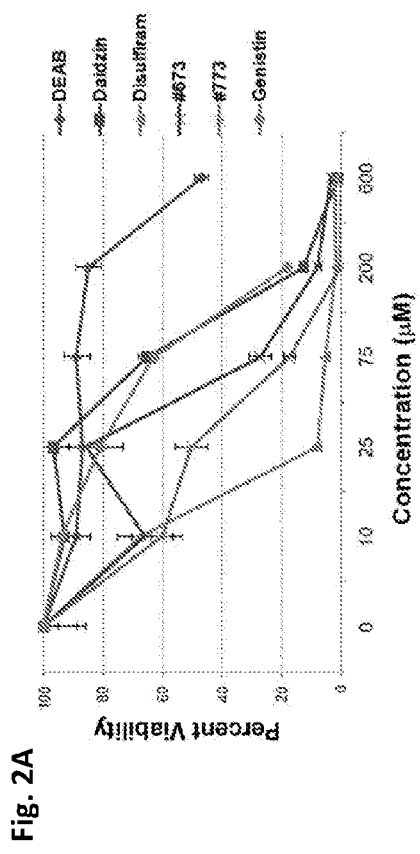
Fig. 2B
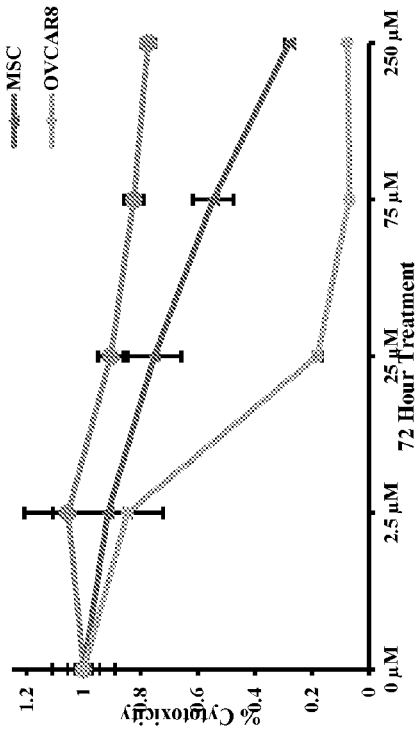
Fig. 2C

Figure 5
Fig. 5A Whole cell line
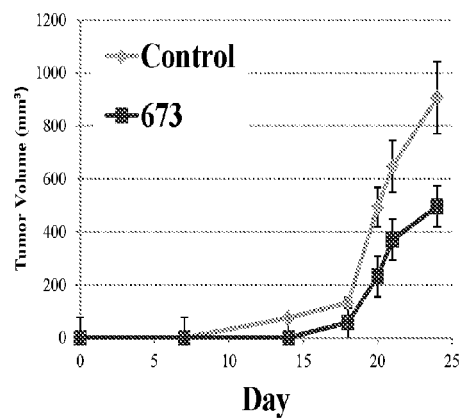
Fig. 5B CD133+ cells
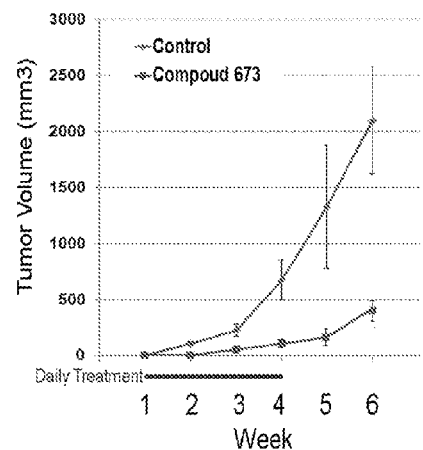
Fig. 5C
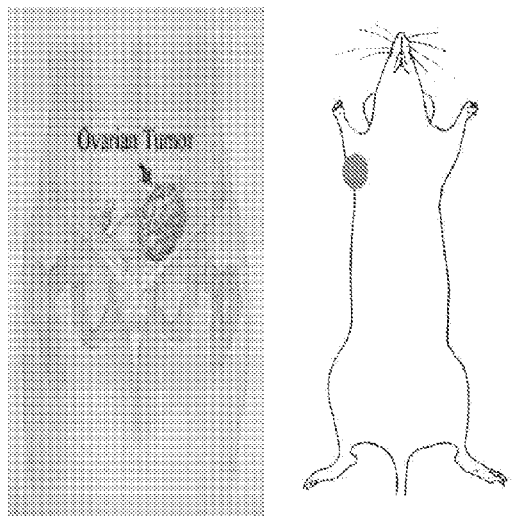
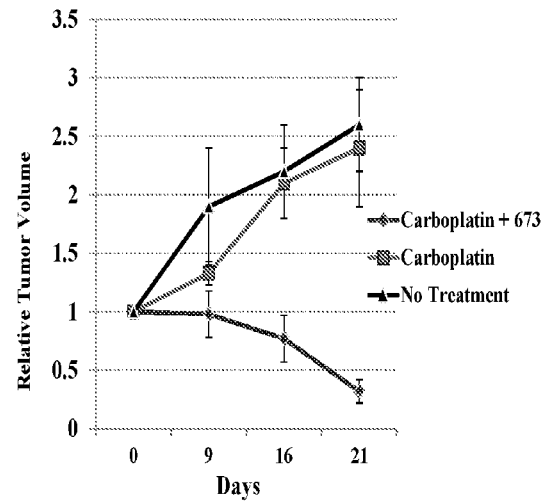

Figure 7
Figure 7A
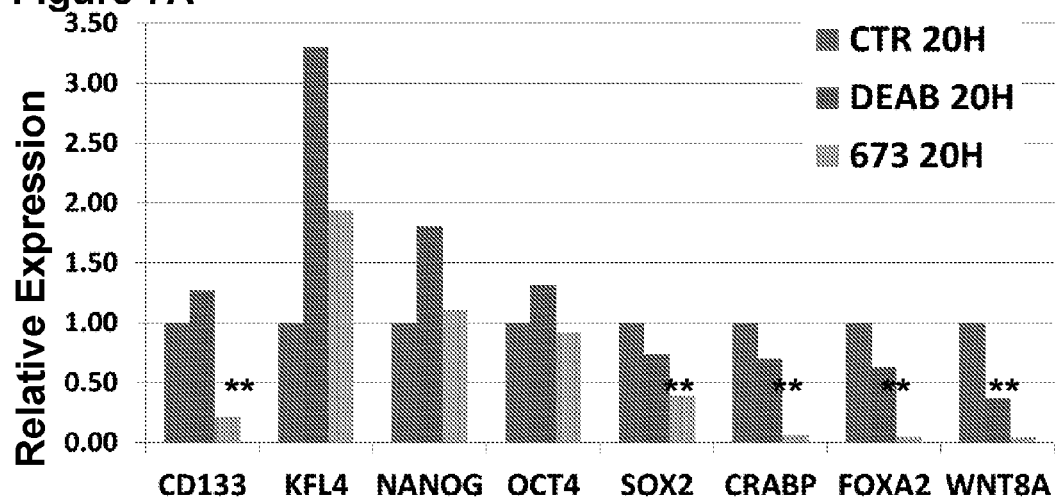
Fig 7B
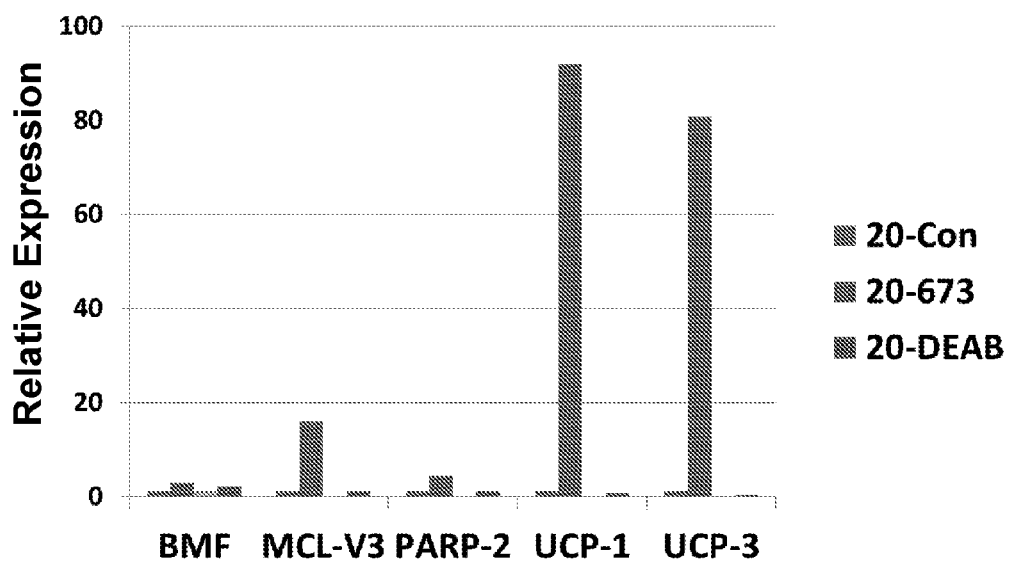

Figure 8 Cont.
Fig. 8B
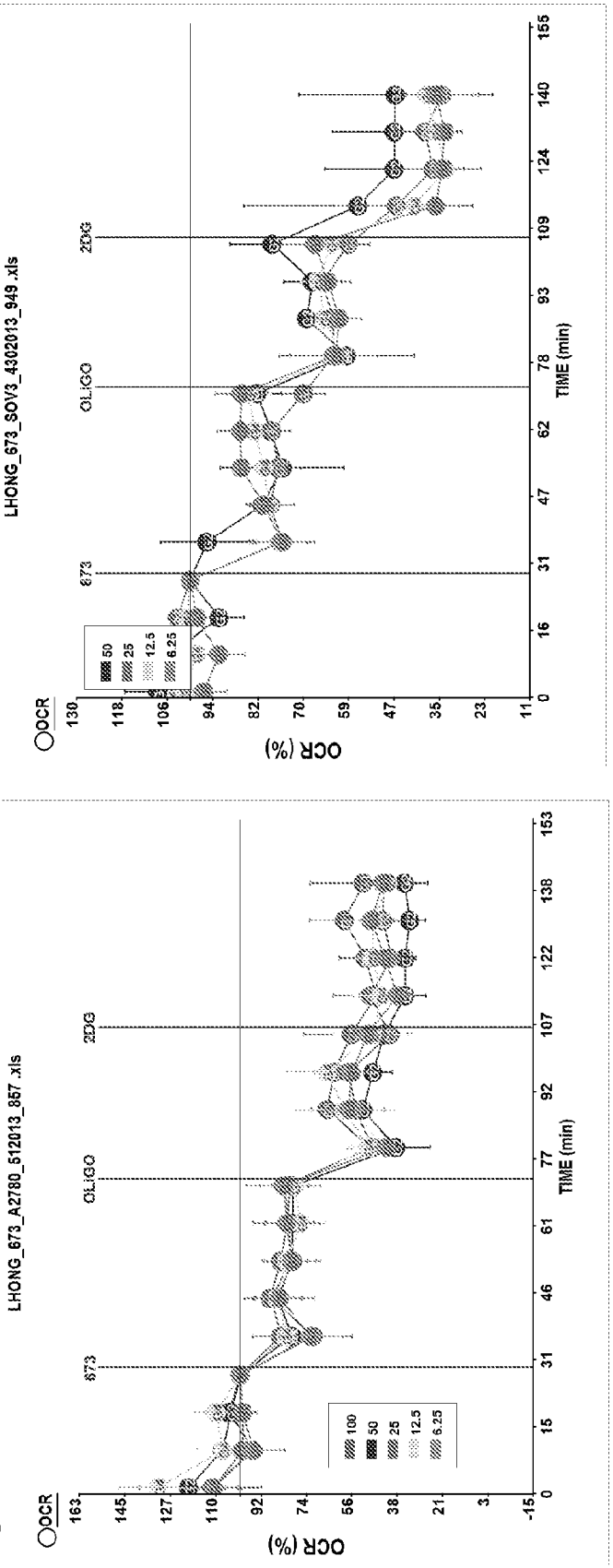
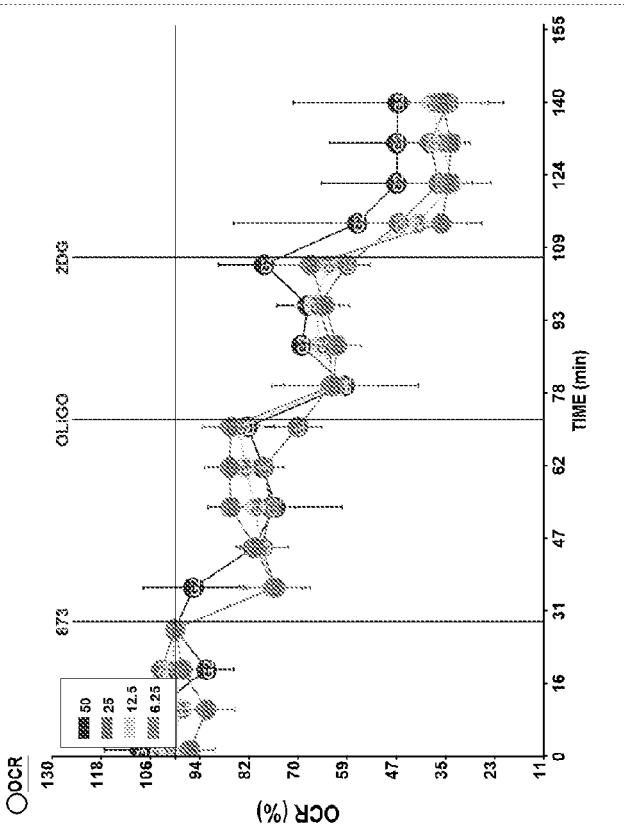

METHODS AND COMPOSITIONS FOR TARGETING CANCER STEM CELLS

CROSS-REFERENCE TO RELATED APPLICATIONS

This application is a national stage of International (PCT) Patent Application Serial No. PCT/US2013/072055, filed Nov. 26, 2013, which claims priority to U.S. Provisional Patent Application Ser. No. 61/730,832 filed Nov. 28, 2012, which is herein incorporated by reference in its entirety.

STATEMENT REGARDING FEDERALLY SPONSORED RESEARCH OR DEVELOPMENT

This invention was made with government support under W81XWH-12-1-0325 awarded by the U.S. Army Medical Research and Material Command. The government has certain rights in the invention.

FIELD OF THE INVENTION

The present invention relates to chemical compounds, methods for their discovery, and their therapeutic and research use. In particular, the present invention provides compounds as therapeutic agents against cancer stem cells.

BACKGROUND OF THE INVENTION

Approximately 22,000 women will be diagnosed with ovarian cancer in 2011 and approximately 15,000 will die of this disease (Edwards et al., J Natl Cancer Inst. 2005; 97:1407-27).

Ovarian cancer symptoms are often vague. Women and their doctors often blame the symptoms on other, more common conditions. By the time the cancer is diagnosed, the tumor has often spread beyond the ovaries. Treatment of ovarian cancer usually involves a combination of surgery and chemotherapy.

While most ovarian cancer patients will have a complete response with surgery and chemotherapy, the majority will relapse and die of their disease. The high relapse rate in ovarian cancer after complete clinical response may be due to a cancer stem cell model in which rare, inherently chemoresistant cancer stem cells capable of proliferating and differentiating to regenerate the various cell types within a tumor, thereby causing relapse of the disease.

Additional treatments for ovarian cancer are needed. Treatment that target cancer stem cells are particularly needed.

SUMMARY

The present invention relates to chemical compounds, methods for their discovery, and their therapeutic and research use. In particular, the present invention provides compounds as therapeutic agents against cancer stem cells.

For example, in some embodiments, the present invention provides a composition comprising one or more compounds that inhibit aldehyde dehydrogenase (ALDH). The present invention is not limited to a particular ALDH inhibitor. In some embodiments, the inhibitors have the structure

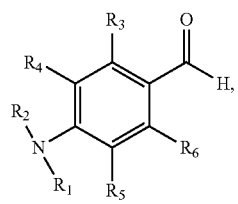

wherein R1 and R2 are independently or together, H, an alkyl, a cycloalkyl, together form a cycloalkyl or heterocyclic alkyl or aryl, an aryl, an alkenyl, a cycloalkyl, alkynl, or a substituted version of the aforementioned groups and R3-R6 are independently a halogen, H, an alkyl, a cycloalkyl, an aryl, an alkenyl, a cycloalkyl, alkynl, or a substituted version of the aforementioned groups. In some embodiments, the inhibitors have the structure

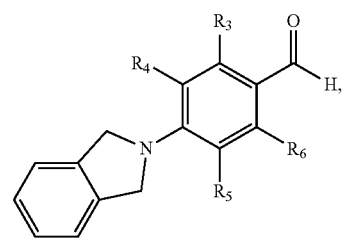

wherein and R3-R6 are independently a halogen, H, an alkyl, a cycloalkyl, an aryl, an alkenyl, a cycloalkyl, alkynl, or a substituted version of the aforementioned groups. In some embodiments, the compounds have the structure

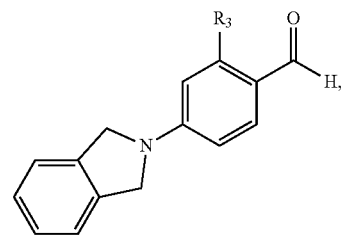

wherein R3 is a halogen, H, an alkyl, a cycloalkyl, an aryl, an alkenyl, a cycloalkyl, alkynl, or a substituted version of the aforementioned groups. In some embodiments, the inhibitor is, for example,

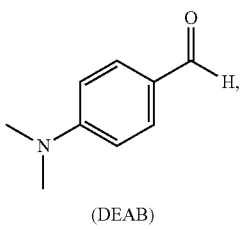

(DEAB)

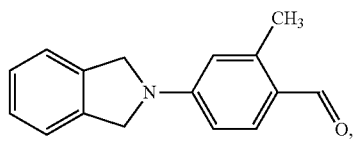

(673A)

-continued

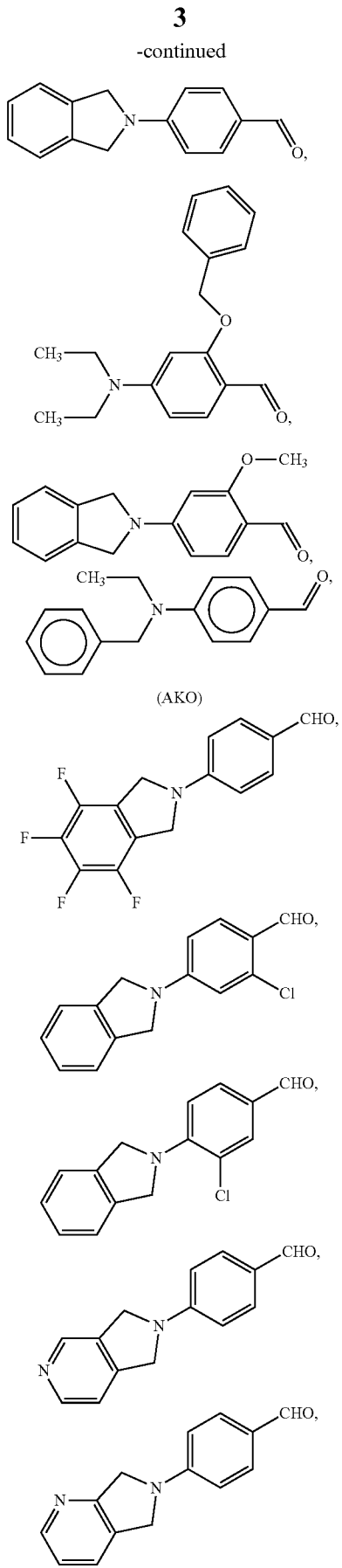

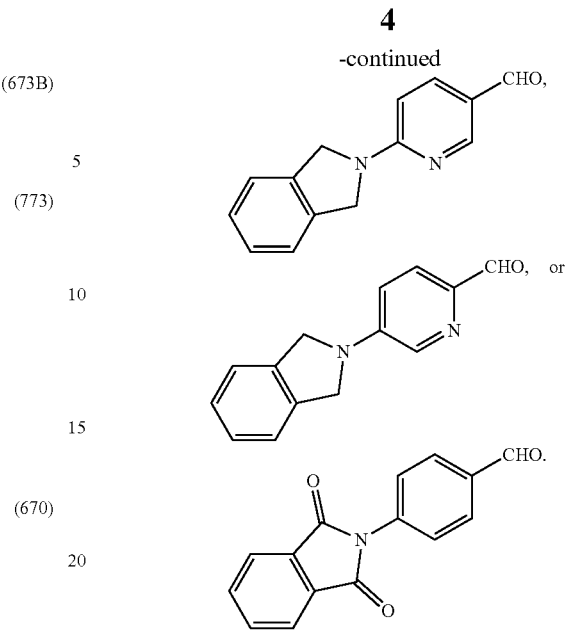

In some embodiments, the inhibitor is a metabolite of any of the aforementioned compounds (e.g.,

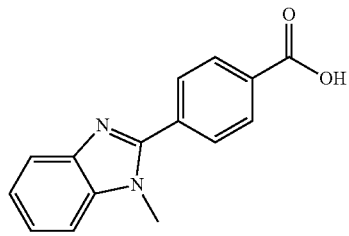 [SMILES: Cn1c(-c2ccc(C(=O)O)cc2)nc2ccccc21]

or a variant thereof). In some embodiments, the composition comprises two or more of the aforementioned compounds. In some embodiments, the composition is a pharmaceutical composition (e.g., comprising a pharmaceutically acceptable carrier). In some embodiments, the composition inhibits ALDH1A1. In some embodiments, the composition kills or inhibits the growth of a cancer stem cell (e.g. an ovarian cancer stem cell). In some embodiments, the composition further comprises a known chemotherapeutic agent (e.g., platinum containing drugs (e.g. cisplatin, carboplatin or oxaliplatin) or taxane drugs (e.g., paclitaxel, docetaxel, and Abraxane). In some embodiments, the composition further comprises an agent that targets cancer stem cells (e.g., an agent that blocks BMP2, IL-6 (e.g., tocilizumab), NOTCH, or DLL4).

The further embodiments, the present invention provides the use of any one of the aforementioned compounds in the treatment of ovarian cancer.

In additional embodiments, the present invention provides a kit comprising a) any one of the aforementioned compounds; and b) a known chemotherapeutic agent (e.g., cisplatin). In some embodiments, the ALDH inhibitor and the known chemotherapeutic agent are in the same or different compositions.

The present invention also provides a method of inhibiting ALDH in a cell, comprising: contacting a cell with any one of the aforementioned compositions under conditions such that the composition kills or inhibits the growth of the cell. In some embodiments, the cell is in vivo. In some embodiments, the cell is a cancer cell (e.g., a cancer stem cells such as an ovarian cancer stem cell). In some embodiments, the cell is in a subject diagnosed with ovarian cancer. In some embodiments, the compound radiosensitizes cancer cells to radiation therapy.

The present invention additionally provides a method of treating ovarian cancer, comprising: administering any one of the aforementioned compounds to a subject diagnosed with ovarian cancer under conditions such that the compound kills or inhibits the growth of the ovarian cancer. In some embodiments, the administering prevents recurrence or metastasis of the ovarian cancer.

Additional embodiments are described herein.

BRIEF DESCRIPTION OF THE DRAWINGS

FIG. 2 shows effect of single agent ALDH inhibitors. A. MTT assay of cytotoxicity of indicated compounds at increasing doses 72 hours after treatment of ovarian cancer cell. B. MTT assay for pancreatic (ASPC and PANC1) and breast cancer (MCF7) cell lines. C. MTT assays of 673 for normal cells (HOSE and MSC) and ovarian cancer (OvCAR8) controls.

FIG. 5 shows the impact of ALDH inhibitor on tumor growth in vivo. A. tumor growth curves for control and 673 treated A2780 tumor cell xenografts. B tumor growth curves for control and 673 treated CD133+ ovarian cancer stem cell initiated tumors. C. Schematic for patient derived xenografts and tumor growth curves demonstrating ALDH inhibitor therapy reverses chemotherapy resistance in a patient derived xenografts.

FIG. 7 shows expression changes associated with ALDH inhibitor therapy. A qRT-PCR for the indicated stem cell genes demonstrating decreased expression of CD133, SOX2, CRABP, and WNT8A. B. qRT-PCR demonstrating increased expression of necrosis associated genes MCL, UCP1 and UCP3.

DEFINITIONS

Figure 1:
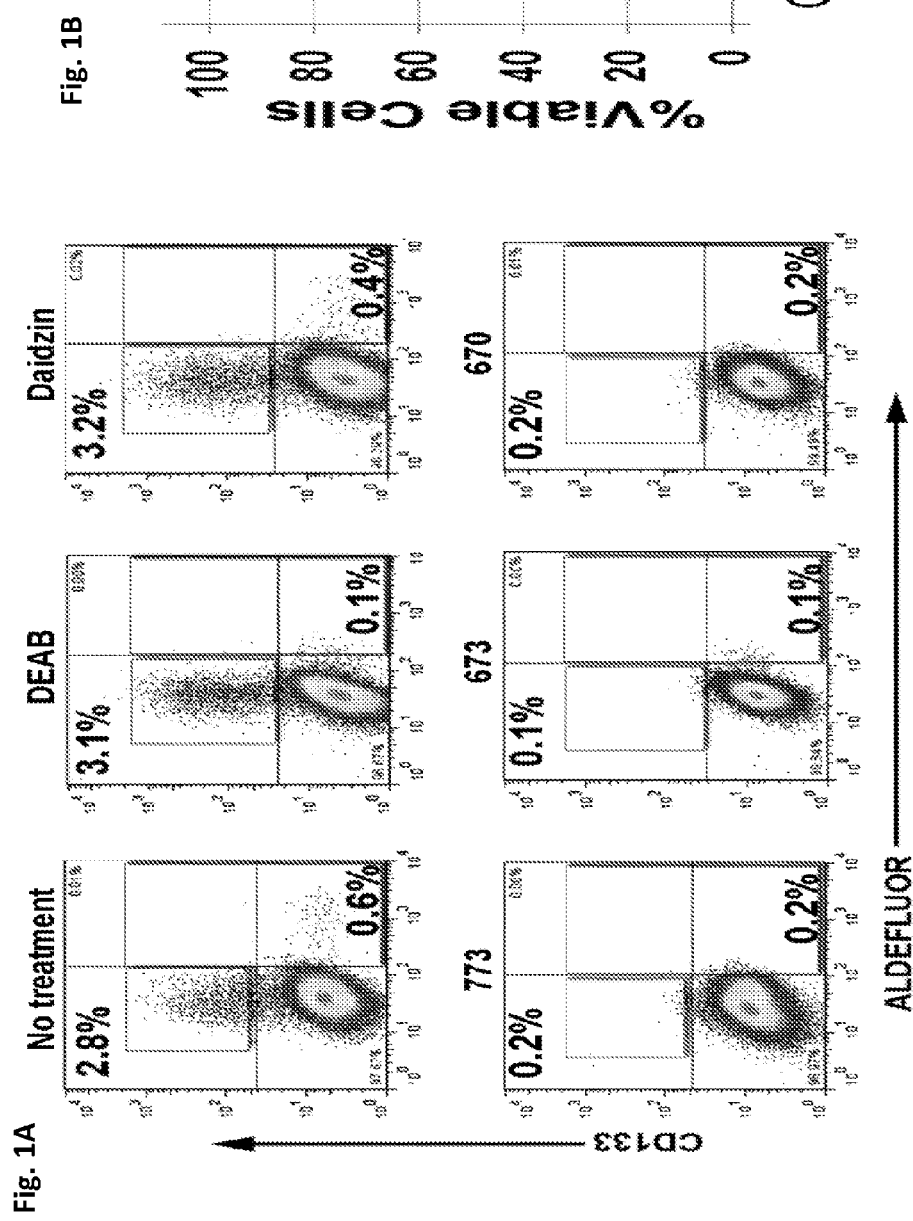
FIG. 1 shows that ALDH inhibitors specifically kill CSC. A. FACS analysis of CD133 and ALDH demonstrating novel ALDH inhibitors lead to a loss of CD133 expressing cells. B. Summation of viability of isolated ALDH+ cells treated with cisplatin or indicated ALDH inhibitors.

To facilitate an understanding of the present invention, a number of terms and phrases are defined below.

As used herein, the term "aliphatic" represents the groups including, but not limited to, alkyl, alkenyl, alkynyl, alicyclic.

As used herein, the term "alkyl" refers to an unsaturated carbon chain substituent group. In general, alkyls have the general formula $C_nH_{2n+1}$. Exemplary alkyls include, but are not limited to, methyl ($CH_3$), ethyl ($C_2H_5$), propyl ($C_3H_7$), butyl ($C_4H_9$), pentyl ($C_5H_{11}$), etc.

As used herein, the term "aryl" represents a single aromatic ring such as a phenyl ring, or two or more aromatic rings (e.g., bisphenyl, naphthalene, anthracene), or an aromatic ring and one or more non-aromatic rings. The aryl group can be optionally substituted with a lower aliphatic group (e.g., alkyl, alkenyl, alkynyl, or alicyclic). Additionally, the aliphatic and aryl groups can be further substituted by one or more functional groups including, but not limited to, chemical moieties comprising N, S, O, —$NH_2$, —$NHCOCH_3$, —OH, lower alkoxy ($C_1$-$C_4$), and halo (—F, —Cl, —Br, or —I).

As used herein, the term "substituted aliphatic" refers to an alkane, alkene, alkyne, or alicyclic moiety where at least one of the aliphatic hydrogen atoms has been replaced by, for example, a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic, etc.). Examples of such include, but are not limited to, 1-chloroethyl and the like.

As used herein, the term "substituted aryl" refers to an aromatic ring or fused aromatic ring system consisting of at least one aromatic ring, and where at least one of the hydrogen atoms on a ring carbon has been replaced by, for example, a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, hydroxyphenyl and the like.

As used herein, the term "cycloaliphatic" refers to an aliphatic structure containing a fused ring system. Examples of such include, but are not limited to, decalin and the like.

As used herein, the term "substituted cycloaliphatic" refers to a cycloaliphatic structure where at least one of the aliphatic hydrogen atoms has been replaced by a halogen, a nitro, a thio, an amino, a hydroxy, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, 1-chlorodecalyl, bicyclo-heptanes, octanes, and nonanes (e.g., norbornyl) and the like.

As used herein, the term "heterocyclic" represents, for example, an aromatic or nonaromatic ring containing one or more heteroatoms. The heteroatoms can be the same or different from each other. Examples of heteroatoms include, but are not limited to nitrogen, oxygen and sulfur. Aromatic and nonaromatic heterocyclic rings are well-known in the art. Some nonlimiting examples of aromatic heterocyclic rings include pyridine, pyrimidine, indole, purine, quinoline and isoquinoline. Nonlimiting examples of nonaromatic heterocyclic compounds include piperidine, piperazine, morpholine, pyrrolidine and pyrazolidine. Examples of oxygen containing heterocyclic rings include, but not limited to furan, oxirane, 2H-pyran, 4H-pyran, 2H-chromene, and benzofuran. Examples of sulfur-containing heterocyclic rings include, but are not limited to, thiophene, benzothiophene, and parathiazine. Examples of nitrogen containing rings include, but not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic ring is optionally further substituted with one or more groups selected from aliphatic, nitro, acetyl (i.e., —C(=O)—CH$_3$), or aryl groups.

As used herein, the term "substituted heterocyclic" refers to a heterocylic structure where at least one of the ring carbon atoms is replaced by oxygen, nitrogen or sulfur, and where at least one of the aliphatic hydrogen atoms has been replaced by a halogen, hydroxy, a thio, nitro, an amino, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to 2-chloropyranyl.

As used herein, the term "electron-rich heterocycle," means cyclic compounds in which one or more ring atoms is a heteroatom (e.g., oxygen, nitrogen or sulfur), and the heteroatom has unpaired electrons which contribute to a 6-π electronic system. Exemplary electron-rich heterocycles include, but are not limited to, pyrrole, indole, furan, benzofuran, thiophene, benzothiophene and other similar structures.

As used herein, the term "linker" refers to a chain containing up to and including eight contiguous atoms connecting two different structural moieties where such atoms are, for example, carbon, nitrogen, oxygen, or sulfur. Ethylene glycol is one non-limiting example.

As used herein, the term "lower-alkyl-substituted-amino" refers to any alkyl unit containing up to and including eight carbon atoms where one of the aliphatic hydrogen atoms is replaced by an amino group. Examples of such include, but are not limited to, ethylamino and the like.

As used herein, the term "lower-alkyl-substituted-halogen" refers to any alkyl chain containing up to and including eight carbon atoms where one of the aliphatic hydrogen atoms is replaced by a halogen. Examples of such include, but are not limited to, chlorethyl and the like.

As used herein, the term "acetylamino" shall mean any primary or secondary amino that is acetylated. Examples of such include, but are not limited to, acetamide and the like.

As used herein, the term "a moiety that participates in hydrogen bonding" as used herein represents a group that can accept or donate a proton to form a hydrogen bond thereby. Some specific non-limiting examples of moieties that participate in hydrogen bonding include a fluoro, oxygen-containing and nitrogen-containing groups that are well-known in the art. Some examples of oxygen-containing groups that participate in hydrogen bonding include: hydroxy, lower alkoxy, lower carbonyl, lower carboxyl, lower ethers and phenolic groups. The qualifier "lower" as used herein refers to lower aliphatic groups (C$_1$-C$_4$) to which the respective oxygen-containing functional group is attached. Thus, for example, the term "lower carbonyl" refers to inter alia, formaldehyde, acetaldehyde. Some non-limiting examples of nitrogen-containing groups that participate in hydrogen bond formation include amino and amido groups. Additionally, groups containing both an oxygen and a nitrogen atom can also participate in hydrogen bond formation. Examples of such groups include nitro, N-hydroxy and nitrous groups. It is also possible that the hydrogen-bond acceptor in the present invention can be the π electrons of an aromatic ring.

The term "derivative" of a compound, as used herein, refers to a chemically modified compound wherein the chemical modification takes place either at a functional group of the compound or backbone.

As used herein, the term "subject" refers to organisms to be treated by the methods of the present invention. Such organisms preferably include, but are not limited to, mammals (e.g., murines, simians, equines, bovines, porcines, canines, felines, and the like), and most preferably includes humans. In the context of the invention, the term "subject" generally refers to an individual who will receive or who has received treatment (e.g., administration of a compound of the present invention and optionally one or more other agents) for a condition characterized by bacterial infection.

The term "diagnosed," as used herein, refers to the recognition of a disease by its signs and symptoms (e.g., resistance to conventional therapies), or genetic analysis, pathological analysis, histological analysis, and the like.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "host cell" refers to any eukaryotic or prokaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "subject is suspected of having cancer" refers to a subject that presents one or more signs or symptoms indicative of a cancer (e.g., a noticeable lump or mass) or is being screened for a cancer (e.g., during a routine physical). A subject suspected of having cancer may also have one or more risk factors. A subject suspected of having cancer has generally not been tested for cancer. However, a "subject suspected of having cancer" encompasses an individual who has received a preliminary diagnosis (e.g., a CT scan showing a mass) but for whom a confirmatory test (e.g., biopsy and/or histology) has not been done or for whom the stage of cancer is not known. The term further includes people who once had cancer (e.g., an individual in remission). A "subject suspected of having cancer" is sometimes diagnosed with cancer and is sometimes found to not have cancer.

As used herein, the term "subject diagnosed with a cancer" refers to a subject who has been tested and found to have cancerous cells. The cancer may be diagnosed using any suitable method, including but not limited to, biopsy, x-ray, blood test, and the diagnostic methods of the present invention. A "preliminary diagnosis" is one based only on visual (e.g., CT scan or the presence of a lump) and antigen tests.

As used herein, the term "cancer cells" refers to individual cells of a cancer. Such cells may include, for example, tumorigenic cells (e.g., capable of generating a tumor), leukemogenic cells (e.g., capable of generating leukemia), cancer stem cells (e.g., capable of forming new tumors or transferring disease upon transplantation into an immunocompromised host), as well as cells that are not tumorigenic, leukemogenic or that are capable of forming new tumors or transferring disease upon transplantation (e.g., mesenchymal and endothelial cells).

"Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

The terms "cancer stem cell," "tumor stem cell," or "solid tumor stem cell" are used interchangeably herein and refer to a population of cells from a solid tumor that: (1) have extensive proliferative capacity; (2) are capable of asymmetric cell division to generate one or more kinds of differentiated progeny with reduced proliferative or developmental potential; and (3) are capable of symmetric cell divisions for self-renewal or self-maintenance. These properties of "cancer stem cells," "tumor stem cells" or "solid tumor stem cells" confer on those cancer stem cells the ability to form palpable tumors upon serial transplantation into an immunocompromised mouse compared to the majority of tumor cells that fail to form tumors. Cancer stem cells undergo self-renewal versus differentiation in a chaotic manner to form tumors with abnormal cell types that can change over time as mutations occur.

As used herein, the terms "stem cell cancer marker(s)," "cancer stem cell marker(s)," "tumor stem cell marker(s)," or "solid tumor stem cell marker(s)" refer to a gene or genes or a protein, polypeptide, or peptide expressed by the gene or genes whose expression level, alone or in combination with other genes, is correlated with the presence of tumorigenic cancer cells compared to non-tumorigenic cells. The correlation can relate to either an increased or decreased expression of the gene (e.g. increased or decreased levels of mRNA or the peptide encoded by the gene).

As used herein, the term "effective amount" refers to the amount of a compound (e.g., a compound of the present invention) sufficient to effect beneficial or desired results. An effective amount can be administered in one or more administrations, applications or dosages and is not limited intended to be limited to a particular formulation or administration route.

As used herein, the term "co-administration" refers to the administration of at least two agent(s) (e.g., a compound of the present invention) or therapies to a subject. In some embodiments, the co-administration of two or more agents/therapies is concurrent. In some embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "toxic" refers to any detrimental or harmful effects on a cell or tissue as compared to the same cell or tissue prior to the administration of the toxicant.

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, and industrial samples. Such examples are not however to be construed as limiting the sample types applicable to the present invention.

As used herein, the terms "purified" or "to purify" refer, to the removal of undesired components from a sample. As used herein, the term "substantially purified" refers to molecules that are at least 60% free, preferably 75% free, and most preferably 90%, or more, free from other components with which they usually associated.

As used herein, the term "modulate" refers to the activity of a compound (e.g., a compound of the present invention) to affect (e.g., to promote or retard) an aspect of cellular function, including, but not limited to, bacterial growth and the like.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., bacterial infection). Test compounds comprise both known and potential therapeutic compounds. A test compound can be determined to be therapeutic by using the screening methods of the present invention. A "known therapeutic compound" refers to a therapeutic compound that has been shown (e.g., through animal trials or prior experience with administration to humans) to be effective in such treatment or prevention. In some embodiments, "test compounds" are agents that modulate apoptosis in cells.

DETAILED DESCRIPTION OF THE INVENTION

The present invention relates to chemical compounds, methods for their discovery, and their therapeutic and research use. In particular, the present invention provides compounds as therapeutic agents against cancer stem cells.

Genetic mouse models of cancer and lineage tracing experiments have confirmed the presence of limited subsets of chemotherapy resistant cancer stem cell (CSC) like cells with multipotent differentiation capacity capable of repopulating tumors after chemotherapy (Schepers et al., Science. 2012; Chen et al., Nature. 2012; Driessens et al., Nature. 2012). The majority of cells in the tumor had limited proliferation capacity (Driessens et al., supra). Furthermore, therapeutics specifically targeting these CSC dramatically improved therapeutic outcome (Chen et al., supra). These studies indicate that CSC represent an important target for therapy.

ALDH is an excellent marker of CSC in both ovarian tumor cell lines and in primary human ovarian cancer tissue (Silva et al., Cancer research. 2011; 71:3991-4001). ALDH+ cells are inherently resistant to chemotherapy and limited numbers of ALDH+ cells initiate tumors, while a 50-fold excess of ALDH(−) tumor cells cannot. Importantly primary human ALDH+ ovarian cancer cells replicate human tumors in mice, generating tumors with both ALDH+ and ALDH− cells. ALDH used in combination with the stem cell marker CD133 enriches CSC isolation. Several other studies support ALDH and CD133 as ovarian CSC markers (Kryczek et al., Int J Cancer. 2011; Deng et al., PLoS One. 2010; 5:e10277; Landen et al., Mol Cancer Ther. 2010; 9:3186-99).

There are 19 known ALDH family members present in the human genome (Koppaka et al., Pharmacol Rev. 2012; 64:520-39; Muzio et al., Free Radic Biol Med. 2012; 52:735-46). These enzymes share limited sequence identity (~30% between ALDH1A and ALDH3A) and exhibit distinct substrate preferences. These enzymes also have distinct critical cellular functions such as regulating reactive oxygen species, retinal (vitamin A) metabolism, lipid oxidation, and resistance to chemotherapy (Koppaka et al. supra). Three of the ALDH isozymes, ALDH1A, ALDH2, and ALDH3A are believed to be responsible for a large majority of measurable ALDH activity. ALDH2 is a mitochondrial enzyme primarily involved in the metabolism of ethanol-derived acetaldehyde, elimination of mitochondrial lipid-peroxidation products and the bio-activation of nitrates. ALDH3A is a cytosolic enzyme which metabolizes aryl aldehydes as well as aldehydes generated by lipid peroxidation. ALDH1A is a cytosolic enzyme that contributes to the biosynthesis of RA through oxidation of retinal. Based on the regulation of RA, ALDH1A indirectly regulates numerous critical cellular processes regulated by RA mediated transcription (Napoli et al., J Steroid Biochem Mol Biol. 1995; 53:497-502). Critical ovarian cancer stem cell genes, such as Nanog and Oct4 are downstream target genes of RA regulated transcription and regulate CSC differentiation (Balmer et al., J Lipid Res. 2002; 43:1773-808). The RA receptor-b (RAR-b) and ALDH3 are also RA target genes, both of which have been linked with the regulation of cellular proliferation rates (Muzio et al., supra Canuto et al., Chem Biol Interact. 2003; 143-144:29-35; Sabichi et al., J Natl Cancer Inst. 1998; 90:597-605).

ALDH1A1 is most strongly implicated as markers of ovarian CSC. In addition to the tumor initiation capacity discussed above, it was found that the presence of ALDH1A1+CD133+ cells in patient's primary tumor specimens correlated with poor outcome (Silva et al., Cancer research. 2011; 71:3991-4001). ALDH1A1 was found to be 100 fold upregulated in ovarian cancer cells that were resistant to either cisplatin or taxanes (Landen et al., Mol Cancer Ther. 2010; 9:3186-99). siRNA knockdown of ALDH1A was toxic to ovarian cancer cells and restored chemosensitivity supporting the role of ALDH1A as a ovarian cancer stem cell target. Similarly, ALDH1A expression by tumor cells was correlated with poor patient outcome (Balmer et al., J Lipid Res. 2002; 43:1773-808). More recently ALDH1A3, ALDH3A2, and ALDH3B have also been reported to be upregulated in ovarian cancer compared to normal ovary (Marchitti et al., J Histochem Cytochem. 2010; 58:765-83; Saw et al., BMC Cancer. 2012; 12:329).

Based on its CSC specific expression and important functional role, ALDH has been supported as a CSC specific therapeutic target (Kast et al., Curr Stem Cell Res Ther. 2009; 4:314-7). CSC targeted therapies are reported to have (i) up to 100-fold increase in relative therapeutic efficacy (Gupta et al., Cell. 2009; 138:645-59), (ii) can reverse resistance to traditional chemotherapeutics (Wei et al., Proc Natl Acad Sci USA. 2010; 107:18874-9), and even (iii) prevent cancer recurrences (Ginestier et al., J Clin Invest. 2010; 120:485-97). Indeed, ALDH inhibitors have been reported to be effective CSC therapy in breast cancer (Yip et al., Br J Cancer. 2011; 104:1564-74). ALDH activators have been reported to enhance stem cell recovery in normal tissue (Banh et al., Clin Cancer Res. 2011; 17:7265-72).

Despite high expression in CSC, ALDH is not essential for normal stem cells. ALDH1A knockout animals were viable with no clear defects (Levi et al., Blood. 2009; 113:1670-80). ALDH1A−/−ALDH3A−/− mice are also viable with only modest defects; the development of cataracts and altered B cell development (Gasparetto et al., Exp Hematol. 2012; 40:318-29 e2). ALDH inhibitors have proven safe for use in patients. Numerous drugs with ALDH inhibitory activity including metronidazole and chloramphenicol have safely been used in patients. Disulfiram is a potent, yet relatively non-selective, ALDH1/2 inhibitor used for the treatment of alcohol addiction (Keung et al., Proc Natl Acad Sci USA. 1993; 90:1247-51). Disulfiram has anti-cancer activity against tumor cell lines in vitro and in animal tumor models in vivo (Kast et al., Curr Stem Cell Res Ther. 2009; 4:314-7, Yip et al., Br J Cancer. 2011; 104: 1564-74, Irving et al., Carcinogenesis. 1987; 8:1309-15; Morrison et al., Melanoma Res. 2010; 20:11-20; Lin et al., Prostate. 2011; 71:333-43). Disulfiram has also been tested in a limited manner clinically. There are currently several ongoing new trials testing Disulfiram as an anti-CSC agent.

Accordingly, embodiments of the present invention provide compositions and methods for treating ovarian cancer (e.g., by targeting ovarian cancer stem cells) with ALDH inhibitors.

I. Inhibitors

As described herein, embodiments of the present invention provide ALDH inhibitors. In some embodiments, compounds target one or more ALDH subtypes (e.g., ALDH1A1). In some embodiments, the inhibitors have the structure

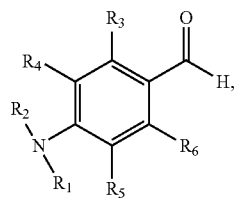

wherein R1 and R2 are independently or together, H, an alkyl, a cycloalkyl, together form a cycloalkyl or heterocyclic alkyl or aryl, an aryl, an alkenyl, a cycloalkyl, alkynl, or a substituted version of the aforementioned groups and R3-R6 are independently a halogen, H, an alkyl, a cycloalkyl, an aryl, an alkenyl, a cycloalkyl, alkynl, or a substituted version of the aforementioned groups. In some embodiments, the inhibitors have the structure

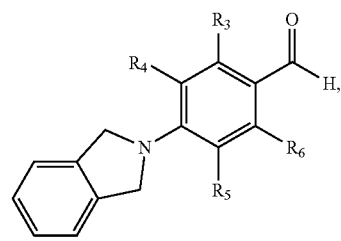

wherein and R3-R6 are independently a halogen, H, an alkyl, a cycloalkyl, an aryl, an alkenyl, a cycloalkyl, alkynl, or a substituted version of the aforementioned groups. In some embodiments, the compounds have the structure

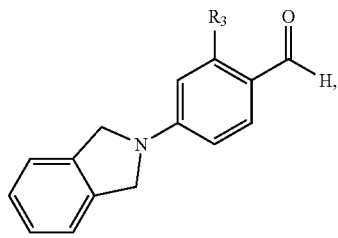

wherein R3 is a halogen, H, an alkyl, a cycloalkyl, an aryl, an alkenyl, a cycloalkyl, alkynl, or a substituted version of the aforementioned groups. In some embodiments, the inhibitor is, for example,

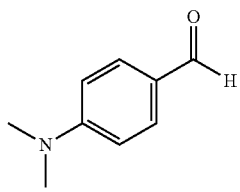

(DEAB; Sigma-Aldrich, St. Louis, Mo.),

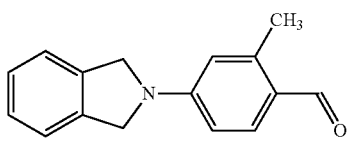 [SMILES: Cc1cc(N2Cc3ccccc3C2)ccc1C=O]

(673A; Chembridge, San Diego, Calif.; Cat. No. 6737540),

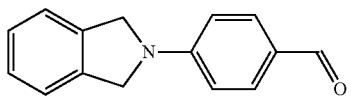 [SMILES: O=Cc1ccc(N2Cc3ccccc3C2)cc1]

(673B; Chembridge, San Diego, Calif.; Cat. No. 6730211)

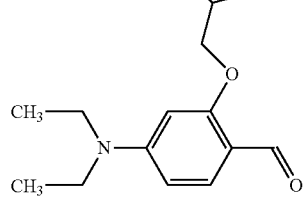

(773; Chembridge, San Diego, Calif.; Cat. No. 7735306),

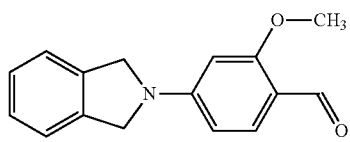 [SMILES: COc1cc(N2Cc3ccccc3C2)ccc1C=O]

(670; Chembridge, San Diego, Calif.; Cat. No. 6702972),

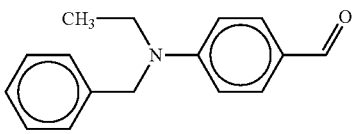

(AKO, Molport, Riga, Latvia),

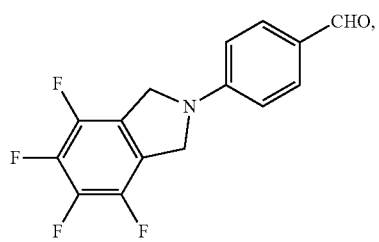

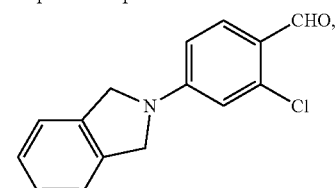

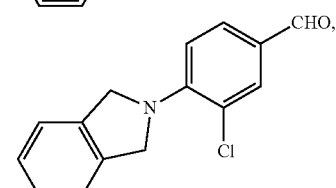

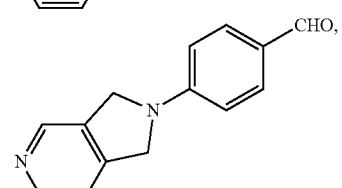

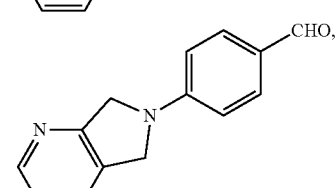

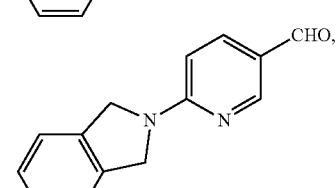

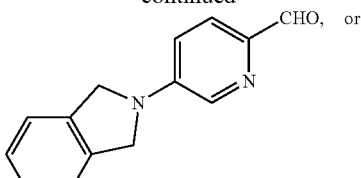

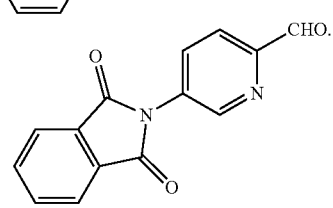

In some embodiments, the inhibitor is a metabolite of any of the aforementioned compounds (e.g.,

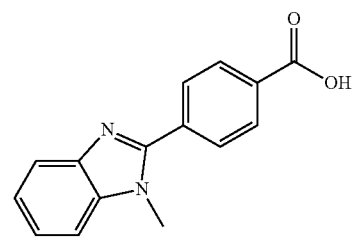 [SMILES: Cn1c(-c2ccc(C(=O)O)cc2)nc2ccccc21]

or a variant thereof). In some embodiments, the inhibitor is a prodrug and the metabolite of the compound is the active agent. In some embodiments, the compound is modified with a label to allow the compound to function as an imaging agent (e.g., radioactively labeled).

The present invention also provides methods of modifying and derivatizing the compositions of the present invention to increase desirable properties (e.g., binding affinity, activity, solubility and the like), or to minimize undesirable properties (e.g., nonspecific reactivity, toxicity, and the like). The principles of chemical derivatization are well understood. In some embodiments, iterative design and chemical synthesis approaches are used to produce a library of derivatized child compounds from a parent compound. In some embodiments, rational design methods are used to predict and model in silico ligand-receptor interactions prior to confirming results by routine experimentation.

II. Pharmaceutical Compositions, Formulations, and Exemplary Administration Routes and Dosing Considerations Exemplary embodiments of various contemplated medicaments and pharmaceutical compositions are provided below.

Embodiments of the present invention provide methods of using the aforementioned compounds in the inhibition of ALDH in cells (e.g., cancer stem cells) and in the treatment of cancers such as, for example, breast cancer, prostate cancer, lung cancer, pancreatic cancer, colon cancer, cervical cancer, uterine cancer, kidney cancer, liver cancer, stomach cancer, esophageal cancer, head and neck cancer, throat cancer, skin cancer, brain cancer (e.g., glioblastoma), testicular cancer, bone cancer, and ovarian cancer. In some embodiments, the cancer is ovarian cancer. In some embodiments, the compounds prevent the recurrence or metastasis of cancer (e.g., by targeting cancer stem cells).

A. Preparing Medicaments

The compounds of the present invention are useful in the preparation of medicaments to treat ovarian cancer. The methods and techniques for preparing medicaments of a compound are well-known in the art. Exemplary pharmaceutical formulations and routes of delivery are described below.

One of skill in the art will appreciate that any one or more of the compounds described herein, including the many specific embodiments, are prepared by applying standard pharmaceutical manufacturing procedures. Such medicaments can be delivered to the subject by using delivery methods that are well-known in the pharmaceutical arts.

B. Exemplary Pharmaceutical Compositions and Formulation

In some embodiments of the present invention, the compositions are administered alone, while in some other embodiments, the compositions are preferably present in a pharmaceutical formulation comprising at least one active ingredient/agent (e.g., ALDH inhibitor), as defined above, together with a solid support or alternatively, together with one or more pharmaceutically acceptable carriers and optionally other therapeutic agents. Each carrier should be "acceptable" in the sense that it is compatible with the other ingredients of the formulation and not injurious to the subject.

Contemplated formulations include those suitable oral, rectal, nasal, topical (including transdermal, buccal and sublingual), vaginal, parenteral (including subcutaneous, intramuscular, intravenous and intradermal) and pulmonary administration. In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then if necessary shaping the product.

Formulations of the present invention suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion. In some embodiments, the active ingredient is presented as a bolus, electuary, or paste, etc.

In some embodiments, tablets comprise at least one active ingredient and optionally one or more accessory agents/carriers are made by compressing or molding the respective agents. In some embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets are made by molding in a suitable machine a mixture of the powdered compound (e.g., active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention are optionally formulated as ointments, creams, suspensions, lotions, powders, solutions, pastes, gels, sprays, aerosols or oils. In alternatively embodiments, topical formulations comprise patches or dressings such as a bandage or adhesive plasters impregnated with active ingredient(s), and optionally one or more excipients or diluents. In some embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions of this invention are constituted from known ingredients in an known manner. This phase typically comprises an lone emulsifier (otherwise known as an emulgent), it is also desirable in some embodiments for this phase to further comprises a mixture of at least one emulsifier with a fat or an oil or with both a fat and an oil.

Preferably, a hydrophilic emulsifier is included together with a lipophilic emulsifier so as to act as a stabilizer. It some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

++

The choice of suitable oils or fats for the formulation is based on achieving the desired properties (e.g., cosmetic properties), since the solubility of the active compound/agent in most oils likely to be used in pharmaceutical emulsion formulations is very low. Thus creams should preferably be a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with suitable base comprising, for example, cocoa butter or a salicylate.

Formulations suitable for vaginal administration may be presented as pessaries, creams, gels, pastes, foams or spray formulations containing in addition to the agent, such carriers as are known in the art to be appropriate.

Formulations suitable for nasal administration, wherein the carrier is a solid, include coarse powders having a particle size, for example, in the range of about 20 to about 500 microns which are administered in the manner in which snuff is taken, i.e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, an include aqueous or oily solutions of the agents.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an agent.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoelic acid), extenders, and stabilizers, etc.

C. Exemplary Administration Routes and Dosing Considerations

Various delivery systems are known and can be used to administer a therapeutic agent (e.g., ALDH inhibitor), e.g., encapsulation in liposomes, microparticles, microcapsules, receptor-mediated endocytosis, and the like. Methods of delivery include, but are not limited to, intra-arterial, intramuscular, intravenous, intranasal, and oral routes. In specific embodiments, it may be desirable to administer the pharmaceutical compositions of the invention locally to the area in need of treatment; this may be achieved by, for example, and not by way of limitation, local infusion during surgery, injection, or by means of a catheter.

The agents identified herein as effective for their intended purpose can be administered to subjects or individuals diagnosed with ovarian cancer. When the agent is administered to a subject such as a mouse, a rat or a human patient, the agent can be added to a pharmaceutically acceptable carrier and systemically or topically administered to the subject.

In some embodiments, in vivo administration is effected in one dose, continuously or intermittently throughout the course of treatment. Methods of determining the most effective means and dosage of administration are well known to those of skill in the art and vary with the composition used for therapy, the purpose of the therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including, but not limited to, oral, rectal, nasal, topical (including, but not limited to, transdermal, aerosol, buccal and sublingual), vaginal, parental (including, but not limited to, subcutaneous, intramuscular, intravenous and intradermal) and pulmonary. It is also appreciated that the preferred route varies with the condition and age of the recipient, and the disease being treated.

In some embodiments, agents are administered intravenously. In some embodiments, agents are formulated in Cremophor (BASF, Parsippany, N.J.)

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient.

Desirable blood levels of the agent may be maintained by a continuous infusion to provide a therapeutic amount of the active ingredient within disease tissue. The use of operative combinations is contemplated to provide therapeutic combinations requiring a lower total dosage of each component antiviral agent than may be required when each individual therapeutic compound or drug is used alone, thereby reducing adverse effects.

D. Exemplary Co-Administration Routes and Dosing Considerations

The present invention also includes methods involving co-administration of the compounds described herein with one or more additional active agents (e.g., known chemotherapeutic agent, e.g., cisplatin). Indeed, it is a further aspect of this invention to provide methods for enhancing prior art therapies and/or pharmaceutical compositions by co-administering a compound of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered chemical agents, biological agents or other treatments may each be administered using different modes or different formulations.

In certain embodiments, the present invention provides method and compositions for co-administration of therapeutics, such as at least one therapeutic that targets cancer stem cells and an anti-neoplastic agent that kills cancer cells. For example, in some embodiments, combination methods provide an ALDH inhibitor in combination with a known chemotherapeutic agent (e.g., platinum containing drugs (e.g. cisplatin, carboplatin or oxaliplatin) or taxane drugs (e.g., paclitaxel, docetaxel, and Abraxane) and/or an agent that targets cancer stem cells (e.g., an agent that blocks BMP2, IL-6 (e.g., tocilizumab), NOTCH, or DLL4).

A wide range of therapeutic agents find use with embodiments of the present invention. Any therapeutic agent that can be co-administered with the agents of embodiments of the present invention, or associated with the agents of the present invention is suitable for use in the methods of the present invention. Some embodiments of the present invention provide methods (therapeutic methods, research methods, drug screening methods) for administering a therapeutic compound of the present invention and at least one additional therapeutic agent (e.g., including, but not limited to, chemotherapeutic antineoplastics, antimicrobials, antivirals, antifungals, and anti-inflammatory agents) and/or therapeutic technique (e.g., surgical intervention, radiotherapies).

Various classes of antineoplastic (e.g., anticancer) agents are contemplated for use in certain embodiments of the present invention. Anticancer agents suitable for use with the present invention include, but are not limited to, agents that induce apoptosis, agents that inhibit adenosine deaminase function, inhibit pyrimidine biosynthesis, inhibit purine ring biosynthesis, inhibit nucleotide interconversions, inhibit ribonucleotide reductase, inhibit thymidine monophosphate (TMP) synthesis, inhibit dihydrofolate reduction, inhibit DNA synthesis, form adducts with DNA, damage DNA, inhibit DNA repair, intercalate with DNA, deaminate asparagines, inhibit RNA synthesis, inhibit protein synthesis or stability, inhibit microtubule synthesis or function, and the like.

In some embodiments, exemplary anticancer agents suitable for use in compositions and methods of the present invention include, but are not limited to: 1) alkaloids, including microtubule inhibitors (e.g., vincristine, vinblastine, and vindesine, etc.), microtubule stabilizers (e.g., paclitaxel (TAXOL), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosphamide, and busulfan (MYLERAN), etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE), etc., and plicamycin (mithramycin), etc.; 4) antimetabolites, including antifolates (e.g., methotrexate, FOLEX, and MEXATE, etc.), purine antimetabolites (e.g., 6-mercaptopurine (6-MP, PURINETHOL), 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines (e.g., 5-fluorouracil (ADRUCIL), 5-fluorodeoxyuridine (FdUrd) (floxuridine)) etc.), and cytosine arabinosides (e.g., CYTOSAR (ara-C) and fludarabine, etc.); 5) enzymes, including L-asparaginase, and hydroxyurea, etc.; 6) hormones, including glucocorticoids, antiestrogens (e.g., tamoxifen, etc.), nonsteroidal antiandrogens (e.g., flutamide, etc.), and aromatase inhibitors (e.g., anastrozole (ARIMIDEX), etc.); 7) platinum compounds (e.g., cisplatin and carboplatin, etc.); 8) monoclonal antibodies conjugated with anticancer drugs, toxins, and/or radionuclides, etc.; 9) biological response modifiers (e.g., interferons (e.g., IFN-α, etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., batimastat, etc.); 17) angiogenesis inhibitors; 18) proteosome inhibitors (e.g., VELCADE); 19) inhibitors of acetylation and/or methylation (e.g., HDAC inhibitors); 20) modulators of NF kappa B; 21) inhibitors of cell cycle regulation (e.g., CDK inhibitors); 22) modulators of p53 protein function; and 23) radiation.

Any oncolytic agent used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |

TABLE 1-continued

| | | |
|---|---|---|
| Allopurinol (1,5-dihydro-4 H-pyrazolo[3,4-d]pyrimidin-4-one monosodium salt) | Zyloprim | GlaxoSmithKline, Research Triangle Park, NC |
| Altretamine (N,N,N',N',N'',N''-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus* Calmette-Gukin [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-, (SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chloroethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1S,3S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |

TABLE 1-continued

| | | |
|---|---|---|
| Docetaxel<br>((2R,3S)-N-carboxy-3-phenylisoserine, N-tert-butyl ester,<br>13-ester with 5b-20-epoxy-12a,4,7b,10b,13a-<br>hexahydroxytax-11-en-9-one 4-acetate 2-benzoate,<br>trihydrate) | Taxotere | Aventis Pharmaceuticals, Inc.,<br>Bridgewater, NJ |
| Doxorubicin HCl<br>(8S,10S)-10-[(3-amino-2,3,6-trideoxy-a-L-lyxo-<br>hexopyranosyl)oxy]-8-glycolyl-7,8,9,10-tetrahydro-<br>6,8,11-trihydroxy-1-methoxy-5,12-naphthacenedione<br>hydrochloride) | Adriamycin, Rubex | Pharmacia & Upjohn<br>Company |
| doxorubicin | Adriamycin PFS<br>Intravenous injection | Pharmacia & Upjohn<br>Company |
| doxorubicin liposomal | Doxil | Sequus Pharmaceuticals, Inc.,<br>Menlo park, CA |
| dromostanolone propionate<br>(17b-Hydroxy-2a-methyl-5a-androstan-3-one propionate) | Dromostanolone | Eli Lilly & Company,<br>Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin<br>((8S-cis)-10-[(3-amino-2,3,6-trideoxy-a-L-arabino-<br>hexopyranosyl)oxy]-7,8,9,10-tetrahydro-6,8,11-<br>trihydroxy-8-(hydroxyacetyl)-1-methoxy-5,12-<br>naphthacenedione hydrochloride) | Ellence | Pharmacia & Upjohn<br>Company |
| Epoetin alfa<br>(recombinant peptide) | Epogen | Amgen, Inc |
| Estramustine<br>(estra-1,3,5(10)-triene-3,17-diol(17(beta))-, 3-[bis(2-<br>chloroethyl)carbamate] 17-(dihydrogen phosphate),<br>disodium salt, monohydrate, or estradiol 3-[bis(2-<br>chloroethyl)carbamate] 17-(dihydrogen phosphate),<br>disodium salt, monohydrate) | Emcyt | Pharmacia & Upjohn<br>Company |
| Etoposide phosphate<br>(4'-Demethylepipodophyllotoxin 9-[4,6-O-(R)-<br>ethylidene-(beta)-D-glucopyranoside], 4'-(dihydrogen<br>phosphate)) | Etopophos | Bristol-Myers Squibb |
| etoposide, VP-16<br>(4'-demethylepipodophyllotoxin 9-[4,6-0-(R)-ethylidene-<br>(beta)-D-glucopyranoside]) | Vepesid | Bristol-Myers Squibb |
| Exemestane<br>(6-methylenandrosta-1,4-diene-3,17-dione) | Aromasin | Pharmacia & Upjohn<br>Company |
| Filgrastim<br>(r-metHuG-CSF) | Neupogen | Amgen, Inc |
| floxuridine (intraarterial)<br>(2'-deoxy-5-fluorouridine) | FUDR | Roche |
| Fludarabine<br>(fluorinated nucleotide analog of the antiviral agent<br>vidarabine, 9-b-D-arabinofuranosyladenine (ara-A)) | Fludara | Berlex Laboratories, Inc.,<br>Cedar Knolls, NJ |
| Fluorouracil, 5-FU<br>(5-fluoro-2,4(1H,3H)-pyrimidinedione) | Adrucil | ICN Pharmaceuticals, Inc.,<br>Humacao, Puerto Rico |
| Fulvestrant<br>(7-alpha-[9-(4,4,5,5,5-penta fluoropentylsulphinyl)<br>nonyl]estra-1,3,5-(10)-triene-3,17-beta-diol) | Faslodex | IPR Pharmaceuticals,<br>Guayama, Puerto Rico |
| Gemcitabine<br>(2'-deoxy-2',2'-difluorocytidine monohydrochloride (b-<br>isomer)) | Gemzar | Eli Lilly |
| Gemtuzumab Ozogamicin<br>(anti-CD33 hP67.6) | Mylotarg | Wyeth Ayerst |
| Goserelin acetate<br>(acetate salt of [D-Ser(But)$^6$, Azgly$^{10}$]LHRH; pyro-Glu-<br>His-Trp-Ser-Tyr-D-Ser(But)-Leu-Arg-Pro-Azgly-NH2<br>acetate [$C_{59}H_{84}N_{18}O_{14}$•$(C_2H_4O_2)_x$ | Zoladex Implant | AstraZeneca Pharmaceuticals |
| Hydroxyurea | Hydrea | Bristol-Myers Squibb |
| Ibritumomab Tiuxetan<br>(immunoconjugate resulting from a thiourea covalent<br>bond between the monoclonal antibody Ibritumomab and<br>the linker-chelator tiuxetan [N-[2-<br>bis(carboxymethyl)amino]-3-(p-isothiocyanatophenyl)-<br>propyl]-[N-[2-bis(carboxymethyl)amino]-2-(methyl)-<br>ethyl]glycine) | Zevalin | Biogen IDEC, Inc.,<br>Cambridge MA |
| Idarubicin<br>(5,12-Naphthacenedione, 9-acetyl-7-[(3-amino-2,3,6-<br>trideoxy-(alpha)-L-lyxo-hexopyranosyl)oxy]-7,8,9,10-<br>tetrahydro-6,9,11-trihydroxyhydrochloride, (7S-cis)) | Idamycin | Pharmacia & Upjohn<br>Company |
| Ifosfamide<br>(3-(2-chloroethyl)-2-[(2-chloroethyl)amino]tetrahydro-<br>2H-1,3,2-oxazaphosphorine 2-oxide) | IFEX | Bristol-Myers Squibb |
| Imatinib Mesilate<br>(4-[(4-Methyl-1-piperazinyl)methyl]-N-[4-methyl-3-[[4-<br>(3-pyridinyl)-2-pyrimidinyl]amino]-phenyl]benzamide<br>methanesulfonate) | Gleevec | Novartis AG, Basel,<br>Switzerland |

TABLE 1-continued

| Drug | Brand | Manufacturer |
|---|---|---|
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperidinopiperidino)carbonyloxy]-1H-pyrano[3',4': 6,7] indolizino[1,2-b] quinoline-3,14(4H,12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((-)-(S)-2,3,5,6-tetrahydro-6-phenylimidazo [2,1-b] thiazole monohydrochloride $C_{11}H_{12}N_2S \cdot HCl$) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Meclorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6 H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5β,20-Epoxy-1,2a,4,7β,10β,13a-hexahydroxytax-11-en-9-one 4,10-diacetate 2-benzoate 13-ester with (2R,3S)-N-benzoyl-3-phenylisoserine) | TAXOL | Bristol-Myers Squibb |
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |

TABLE 1-continued

| | | |
|---|---|---|
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6 H-purine-6-thione) | Thioguanine | GlaxoSmithKline |
| Thiotepa (Aziridine,1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4': 6,7] indolizino [1,2-b] quinoline-3,14-4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxyl]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

III. Drug Screens

In some embodiments of the present invention, the compounds of the present invention, and other potentially useful compounds, are screened for their biological activity (e.g., ability to block ALDH).

In some embodiments, structure-based virtual screening methodologies are contemplated for identifying ALDH inhibitors. For example, in some embodiments, molecular modeling is used to identify inhibitors. In some embodiments, modeling is used to identify compounds that inhibit the activity of ALDH or ALDH pathway components.

In some embodiments, compounds are screened in cell culture or in vivo (e.g., non-human or human mammals) for their ability to inhibit ALDH. In some embodiments, screens detecting expression or inhibition of expression of downstream signaling molecules.

In some embodiments, the present invention provides high throughput screening of test compounds. For example, in some embodiments, large numbers of different test compounds (e.g., from a test compound library) are provided (e.g. attached to or synthesized) on a solid substrate. Test compounds can be reacted with cancer stem cells, or portions thereof, and washed. Bound cancer stem cells are then detected by methods well known in the art, using commercially available machinery and methods (e.g., the Automated Assay Optimization (AAO) software platforms (Beckman, USA) that interface with liquid handlers to enable direct statistical analysis that optimizes the assays; modular systems from CRS Robotics Corp. Burlington, Ontario), liquid handling systems, readers, and incubators, from various companies using POLARA (CRS), an open architecture laboratory automation software for a Ultra High Throughput Screening System; 3P (Plug&Play Peripherals) technology, which is designed to allow the user to reconfigure the automation platform by plugging in new instruments (ROBOCON, Vienna, Austria); the Allegro system or STACCATO workstation (Zymark), which enables a wide range of discovery applications, including HTS, ultra HTS, and high-speed plate preparation; MICROLAB Vector software (Hamilton Co., Reno, Nev., USA) for laboratory automation programming and integration; and others).

In some embodiments, assays measure a response the target cells (cancer stem cells or genetically modified cancer stem cells) provide (e.g., detectable evidence that a test compound may be efficacious). In some embodiments, the detectable signal is compared to control cells and the detectable signal identified by subtraction analysis. The relative abundance of the differences between the "targeted" and "untargeted" aliquots can be simultaneously compared (e.g., using a "subtraction" analysis (differential analysis) technique such as differential display, representational difference analysis (RDA), GEM-Gene Expression Microarrays (U.S. Pat. No. 5,545,531), suppressive subtraction hybridization (SSH) and direct sequencing (PCT patent application WO 96/17957). The subtraction analysis can include the methods of differential display, representational differential analysis (RDA), suppressive subtraction hybridization (SSH), serial analysis of gene expression (SAGE), gene expression microarray (GEM), nucleic acid chip technology, or direct sequencing).

EXAMPLES

The following examples are provided to demonstrate and further illustrate certain embodiments of the present invention and are not to be construed as limiting the scope thereof.

Example 1

Material and Methods

Cell Lines and Cytotoxic Assays

A2780 and OVCAR8 ovarian cancer cell line was obtained from Dr. Susan Murphy (Duke University, Durham, N.C.) and SKOV3 cells were obtained from Dr. Rebecca Liu (University of Michigan, Ann Arbor, Mich.). $2 \times 10^5$ A2780 cells were plated in 6-well plates in RMPI-10 (10% fetal bovine and 1% streptomycin/penicillin (Invitrogen)) and incubated in 37° C. 5% $CO_2$ in air mixture for 24 hours. Cells were then treated with incremental doses of 673 or 12.5 µM for 24-72 hours. Evaluation of viability was performed with tryptan blue and the Countess.

Flow Cytometry and Fluorescence-Activated Cell Sorting (FACS)

Cells from human ovarian cancer cell lines (A2780, OVCAR8, or SKOV3), human ascites, or primary ovarian tumors were counted in single cell suspensions. All results were analyzed using Summit 6.0 (Beckman Coulter, Inc.)

Tumor Processing

Informed consent was obtained from patients for tissue procurement in accordance with the protocol approved by the University of Michigan's Institutional Review Board. All tumors obtained were stage III or IV epithelial ovarian, fallopian tube, or primary peritoneal cancer of serous histology. Fresh tumor specimens were minced and processed into single-cell suspensions, and isolated on a ficol gradient as previously described [Pulaski 2009]. For ascites samples, cells were isolated via centrifugation, and red cells lysed using ACK buffer (Lonza Walkersville Inc.).

Tumor Sphere Assays

Tumor associated ascites cells were isolated by centrifugation and treated with ACK lysis buffer (Fischer Scientific). 5000 cells were placed in each well of the 6-well ultra-low adherence plates (Corning, Acton, Mass., USA) with 3 ml of supplemented MEBM (Lonza). After 24 hours, cells were treated with either media alone or UM #673. Media was added every 3-4 days, and all tumor sphere counts were done at 2 weeks. Alternatively, sphere assays were also performed with cancer cell lines A2780 and OVCAR8. Cells in culture were trypsinized and 2000 cells were either directly placed or FACS isolated for CD133+ and CD133− cells before plating in wells of ultra-low adherence plates. Images of spheres were photographed using the Olympus Microsuite Biological suite Software.

Animal Studies 6-8 week old nude female mice were purchased from Charles River Laboratories. All xenograft experiments were performed with approval of the University Committee on Use and Care of Animals of the University of Michigan. To generate tumors, $7.5 \times 10^4$ unsorted A2780 cells or 7500 CD133+ sorted A2780 cells were combined with 100 µl of DPBS and 100 µl of Matrigel (BD Biosciences), and then implanted subcutaneously into bilateral axillae of each mouse. 3 days after inoculation with tumors, mice were given an intra-peritoneal injection of (1) control DMSO 40 µl, (2) Cisplatin 250 µg/ml, (3) UM #673 10 µM, or (4) Cisplatin plus UM #673 (n=9 mice per treatment group). Tumor growth was measured using calipers, and tumor volume was calculated based on the modified ellipsoid formula (L×W×W/2), where L is the length and W is the width of the tumor. The mice were euthanized when tumors reached 1.5 to 2 $cm^3$ and animal safety euthanasia guidelines were met. Intraperitoneal tumors were generated using $5 \times 10^6$ OVCAR8 in 250 ml of PBS and injected I.P. 3 days after inoculation, mice were given intra-peritoneal injection of Cisplatin or Cisplatin plus UM #673.

Immunohistochemistry

Fresh murine tumors were embedded in OCT media and placed in −80° C. freezer. Tumor blocks were cut to 8 microns sections on the Microm550 cryostat and placed on slides. The slides were dried overnight in room temperature, fixed in Acetone, blocked using horse serum, and primary antibody staining with either with anti-Ki67 or mouse-CD31 antibody. CD31+ blood vessels and Ki67+ cells were counted from # high-power fields (100×) per section.

MTT 7500 of HOSE, MSC, and OVCAR8 cells were plated on a 96-well plate and rested for 24 hours. They were then treated with incremental doses of 673 for 72 hours. They were then analyzed according to the Vybrant® MTT Cell Proliferation Assay Kit (Invitrogen).

TEM $2\times10^6$ A2780 cells were plated on 60 mm$^2$ and rested overnight followed by no treatment, 12.5 µM of UM #673 for 12 hours, or 25 µM of UM #673 for 18 hours. Cells were then washed with a phosphate buffer and fixed with glutaraldehyde. The samples were then processed, stained, and cut at the University of Michigan histology core. Images were obtained through Philips CM-100 Transmission Electron Microscope.

Statistical Analysis p values of less than 0.5 were considered statistically significant. A 2-tailed student t-test was used.

Results

UM673 is an ALDH1A1 Specific Inhibitor

Several compounds with molecular analogy to the ALDH inhibitor DEAB were screened for their ability to eliminate ovarian CSC. A2770 cells, a cancer cell line for which both ALDH and CD133 have been demonstrated to be markers of CSC were treated. A compound, UM673, that resulted in both reductions in not only ALDH+ cells, but also CD133+ cells (FIG. 1A) was identified. In order to determine if the loss of CD133 or ALDH expressing cells is due to down-regulation/loss of enzyme function or due to cell death, FACS isolated CD133+ or ALDH+ cells were treated as single cells in microfluidic culture. 673 treatment was associated with the death of ~93% of CD133+ cells and 65% death of ALDH+ cells (FIG. 1B).

In vitro enzymatic inhibition assays ALDH1A1, ALDH1A2, ALDH1A3, ALDH2, and ALDH3A1 demonstrated that compound UM 673 is a selective ALDH1A1 inhibitor. UM673 demonstrated an IC50 of <230 nm for all the ALDH1A isoforms with >2 uM for the other ALDH isoforms (Table 1).

In order to confirm that ALDH1A1 and ALDH1A3 are primary targets of UM673, siRNA knockdown studies were performed. Similar to treatment with UM673, ALDH1A1 and ALDH1A3, siRNA knockdown was associated with a decrease in the percentage of CD133+ cells. Combined ALDH1A1 and ALDH1A3 knockdown was partially additive with the greatest reductions in CD133+ cells. Similarly, ALDH1A1 knockdown was synergistic with chemotherapy as previously reported.

Antineoplastic Effects of Novel ALDH Inhibitor UM#673

MTT assays were first performed with increasing doses of UM673 on several ovarian cancer cell lines including A2780, SKOV3, and OvCAR8 (FIG. 2A). TD50 ranged from 12-50 uM. Measurable effects on A2780 viability were observed as low as 2.5 µM. Toxicity was screened versus pancreatic cancer cell lines and breast cancer cell lines. Once again versus bulk populations, variable modest cytotoxicity was observed. The toxicity of these compounds versus normal human ovarian surface epithelial cells and healthy adipose derived mesenchymal stem cells was assayed. Very little toxicity was observed with TD50 of ~105 uM for each cell line.

Figures 3, 3A, 3B:
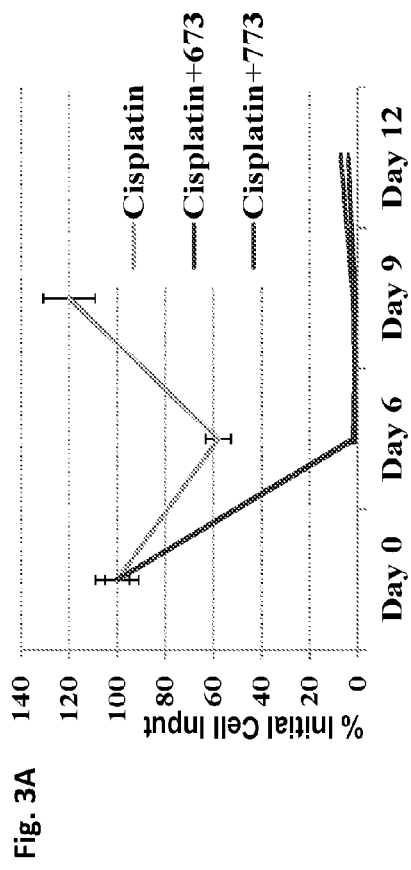
FIG. 3 shows that ALDH inhibitors synergize with chemotherapy. A. Time to recovery for SKOV3 ovarian cancer cells treated with cisplatin or combined cisplatin and ALDH inhibitor. B. Time to recovery for purified ALDH+ and ALDH(−) cells treated with cisplatin alone or combined with ALDH inhibitor

To further demonstrate the anti-CSC activity of UM673, isolated ALDH+ and ALDH− cells were treated with either cisplatin alone or cisplatin plus UM673 (FIG. 3A). Cisplatin treated ALDH+ cells required approximately 6 days to recover whereas cisplatin treated ALDH− cells required 14 days to recover. In contrast, ALDH+ cell treated concurrently with cisplatin and UM673 required 21 days to recover back to initial cell levels. ALDH− cells treated concurrently with cisplatin and showed no additive benefit suggesting selectivity for the ALDH+ cells.

UM #673 Functionally Restricts OvCSC Activity.

Figure 4:
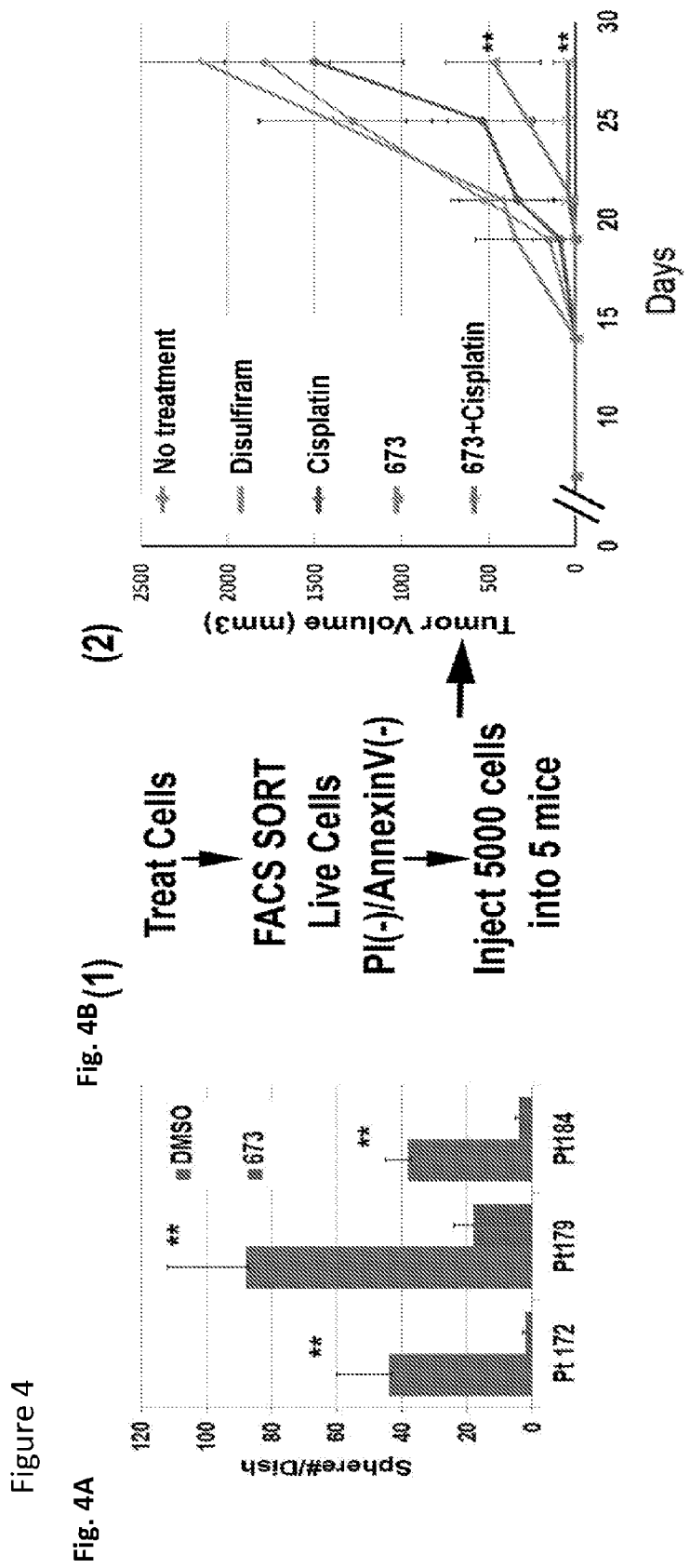
FIG. 4 shows that ALDH inhibitors functionally deplete CSC activity. A. tumor spheres formed from primary patient derived ovarian cancer cells with DMSO (control) and 673 ALDH inhibitor treatment. B. tumor growth curves from 5000 cells isolated following the indicated treatments, demonstrating 673 treatment alone or together with cisplatin reduces tumor initiation and growth.

In order to further characterize UM #673 activity targeting OvCSC, a functional CSC assay was performed. Tumor sphere forming assays were performed with both FACS isolated CD133+A2780 cells and OVCAR8 cells (a cell line with >90% CD133 expression). A single treatment with 10 µM of UM #673 in the CD133+ sorted A2780 cells resulted in a 2.6 fold decrease in sphere number and a nearly 8-fold reduction in total cell number. Treatment of OVCAR8 cells resulted in a 5.6 fold decrease in sphere formation and a 3 fold reduction total cell numbers. This assay was repeated using primary human ovarian cancer associated ascites cell from three patients. Treatment with 673 was associated with an average of 7.3 fold (range 4-50) reduction in the number of spheres formed (FIG. 4A).

An important functional aspect of a cancer stem cell is the ability to initiate tumors with limited cell numbers. In order to determine if UM673 could impact tumor initiation, cells were treated in vitro with a single dose of UM673 alone or in combination with cisplatin. Cells were allowed to recover for three days and then PI(−)/Annexin(−) live cells were faxed isolated and injected into mice. 200, 1000, or 5000 cells from each treatment group (n=4-10/group) were injected. As a single agent neither cisplatin or UM673 affected tumor initiation compared to untreated controls (Table 1; FIG. 4B). However when used in combination cisplatin and UM673 eliminated all tumor initiating capacity (Table 1). This was seen at all cellular titrations. Taken together this data indicated that UM673 either eliminates or chemo sensitizes chemotherapy resistant OvCSC.

UM673 antineoplastic effect in vivo.

The impact of UM673 as a single agent was evaluated. NOD/SCID mice were inoculated with $1\times10^5$ unsorted A2780 cells and treatment was initiated three days after tumor inoculation with either vehicle control or UM #673. Treatment with UM673 resulted in a statistically significant reduction in tumor growth, though did not eliminate tumors (FIG. 5A).). Greatest activity was seen when isolated CD133+ cancer stem cells were used to initiate tumors (FIG. 5B). This is consistent with other studies of CSC targeting agents.

The experiments were repeated in combination with cisplatin. In addition, xenografts from both whole cell line and FACS isolated CD133+ cells were treated. While single agent therapy with both cisplatin and UM 673 demonstrated modest restrictions in tumor growth, concurrent therapy led a 4-fold reduction in tumors. Indicating a stem cell selective activity for UM673 greatest therapeutic benefit was observed in the tumor xenografts generated from isolated CD133+ cells.

In order to confirm in vivo activity against primary ovarian cancers, primary human tumor xenografts were generated from a patient with chemotherapy refractory ovarian cancer. Xenografts were allowed to grow until they reached ~500 mm$^3$, and then treatment with either vehicle, cisplatin or cisplatin and UM 673 was initiated. While cisplatin therapy alone had no effect on tumor growth, concurrent therapy resulted in tumor regression. Maintenance of UM673 therapy alone prevented tumor regrowth. After discontinuation of therapy, tumor regrowth was observed after approximately 4 weeks (FIG. 5D).

UM673 Induces Karyolysis and Necrosis.

Figure 6:
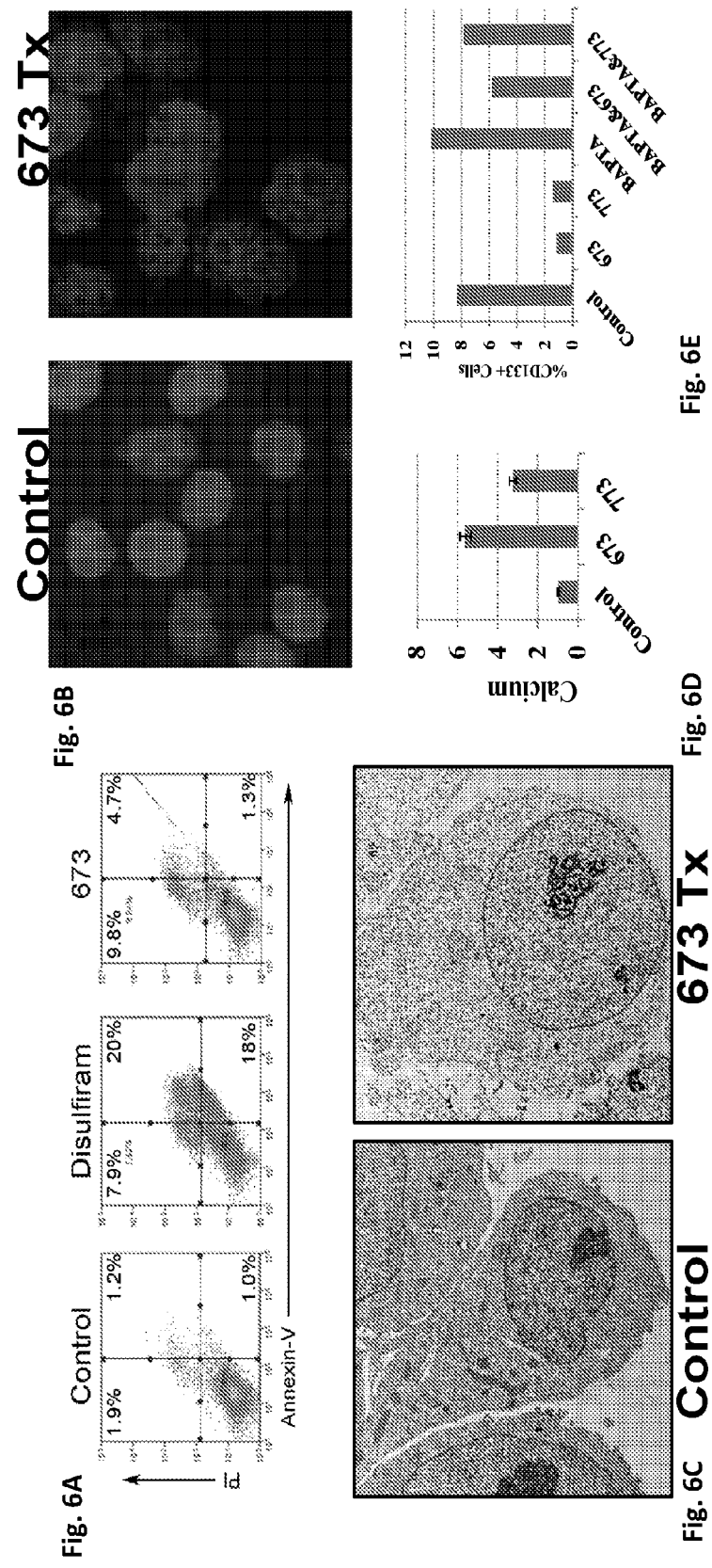
FIG. 6 shows that ALDH inhibition induces necrosis in CSC. A. FACs analysis for annexin-V and PI stain of control, disulfiram, and 673 treated cells demonstrating no induction of apoptosis by 673 treatment. B immunofluorescence demonstrating swollen, lytic nuclei with ALDH inhibitor treatment. C electron micrographs demonstrating ALDH Inhibitor therapy results in, cellular, mitochondrial and nuclear swelling consistent with necrosis. D. compilation of FACS demonstrating ALDH inhibitors result in intracellular calcium increases. E compilation of facts results demonstrating The calcium scavenger BAPTA can abrogate necrotic cell death of CD133+ cells.
Figures 8, 8A:
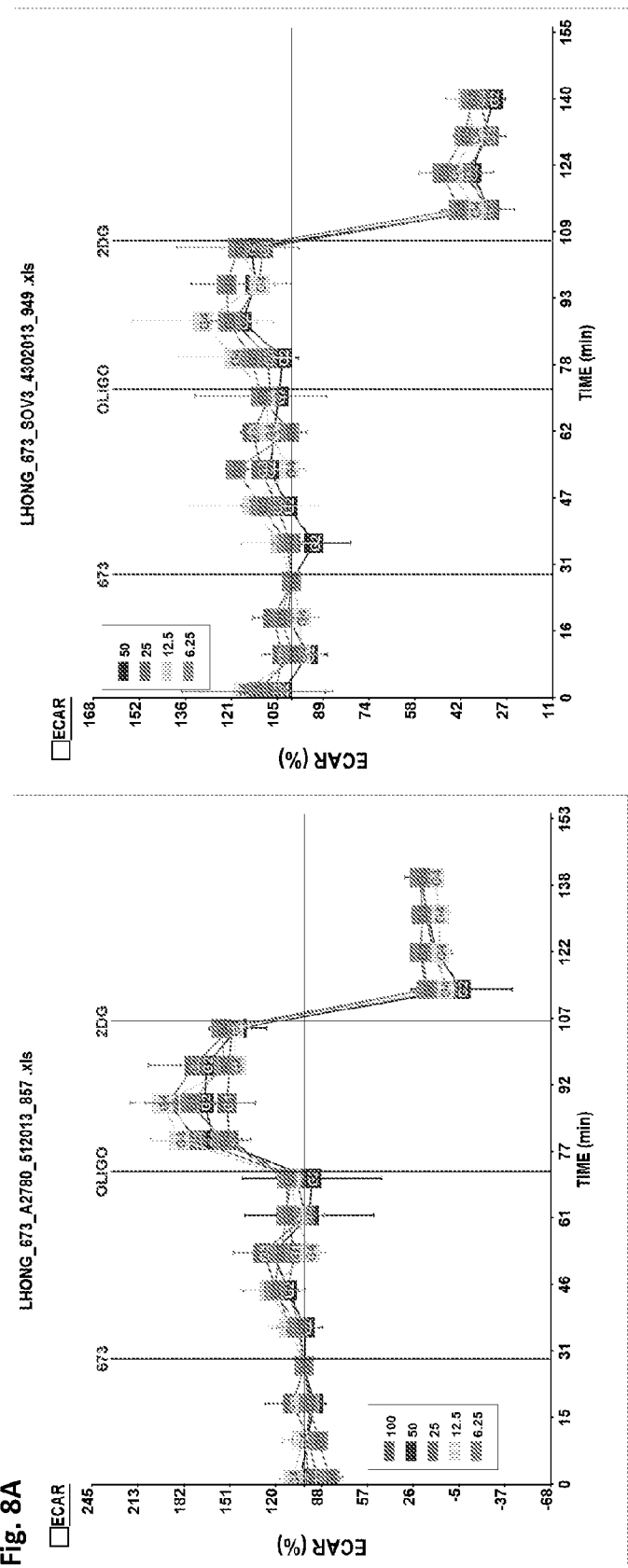
FIG. 8 shows the impact of ALDH inhibition on cellular metabolism. A. ALDH inhibitor therapy has no impact on extracellular acidification (ECAR)/cellular glycolysis. B. ALDH inhibitor therapy reduces oxygen Consumption suggesting mitochondrial defects.

Next, the mechanism whereby UM673 induces OvCSC cell death was investigated. PI/Annexin-V FACS analysis of UM673 treated cells was performed to determine if cells were undergoing apoptosis. Treatment with 673 was not associated with an increase in Annexin-V staining in cells suggesting apoptosis was not the primary mechanism of cell death (FIG. 6A). Further supporting this, use of the pan-caspase inhibitor ZVAD-FMK had no impact on UM673 induced reductions in CD133+ cell counts.

Cellular histology was evaluated 24 hours after treatment with UM 673. Fluorescent images of DAPI labeled cells demonstrated that treatment with UM 673 results in nuclear swelling and loss of DNA in a manner consistent with karyolysis and program cell necrosis (FIG. 6B). Light microscopy images of 0.5 micron sections stained with toluidine blue helps to confirm the presence of fragmented nuclei and loss of cell architecture with treatment. In order to determine whether the nuclear findings on fluorescent microscopy images were truly karyolysis, a distinct nuclear process associated with necrosis, transmission electron microscopy was performed. Once again cells treated with UM #673 demonstrated findings consistent with necrosiss (FIG. 6C). In comparison to controls, there is evidence of cell enlargement and swelling. There is an increase in the translucency of the cytoplasm, as well as mitochondria swelling and loss of architecture. In the nucleus, the presence of fragmented chromatin is seen secondary to nuclear DNAse. With higher dose of UM #673, rupture of plasma membrane with spilling of cytoplasmic contents is evident.

Program cell necrosis associated with the nuclear cytoplasmic shuttling of the protein HMBG1. Immunofluorescent analysis of HMBG1 protein with 673 treated cells demonstrated clear relocalization of HMBG1.

Programmed cell necrosis is known to be linked with decreases in cellular ATP and an increase in intracellular calcium. Using fluorescent analysis of intra-cellular calcium, treatment with UM 673 was associated with a fourfold increase in intracellular calcium (FIG. 6D). Furthermore, reduction in CD 133 positive cells with UM 673 treatment could be partially abrogated by the calcium scavenging compound BAPTA (FIG. 6E). As program cell necrosis is known to be activated via the RIP kinases, the impact of the RIP kinase inhibitor necrostatin was evaluated. Necrostatin treatment could only partially abrogate the effects of UM673, indicating that UM673 may be inducing necrosis in part in a RIP kinase independent manner.

UM673 and Retinoic Acid Signal Transduction and Metabolism.

ALDH1A isoforms are the primary members of the 'retinaldehyde' subgroup of aldehyde dehydrogenases. Retinaldehydes play a primary role in the biosynthesis of retinoic acid and thereby regulate retinoic acid mediated transcription. Retinoic acid transcription changes in cells treated with UM673 were assayed. It was observed that numerous important stem cell factors including Oct4, and Sox2 were down regulated upon treatment with UM673 (FIG. 7A). 80× induction of the mitochondrial uncoupling proteins UCP1 and UCP3 was observed (FIG. 7B).

UCP1 and UCP3 proteins play a critical role in cellular metabolism. The impact of UM673 on cellular metabolism was evaluated. SeaHorse studies demonstrated that UM673 treatment was associated with a slow and steady decline in cellular oxygen consumption. Treatment with oligomycin, which promotes glycolysis, was associated with an appropriate increase in extracellular acidification, indicating UM673 is not primarily impacting glycolysis. In contrast the addition of two deoxy glucose have minimal further reductions in oxygen consumption, indicating UM673 act primarily at the mitochondria.

To directly assess cellular metabolism of the mitochondria, LCMS was performed in control and UM673 treated cells. Consistent with reduced mitochondrial metabolism, a decrease in the ratio of ATP:ADP and ATP:AMP was observed. No significant change in the ratio of NADH:NAD was observed, indicating an early blockage in the Krebs cycle. A marked decrease in the levels of citrate with UM673 treatment and a decrease in downstream molecules including a decrease in succinate and malate was observed.

Finally, to determine if UM673 induction of UCP1 or UCP3 resulted in the observed metabolic defects and program cell necrosis, UCP1 was overexpressed into several ovarian cancer cell lines.

The present example describes the identification of a novel ALDH1A1 specific inhibitor which selectively induces necrotic cell death of ovarian cancer stemlike cells. This compound demonstrates minimal toxicity towards normal cells in vitro, and no toxicity in vivo. As a single agent this compound has modest antitumor activity. However this compound is highly synergistic with chemotherapy and rude versus chemotherapy resistance in vivo.

siRNA knockdown of ALDH1A1 in ovarian cancer, breast cancer, and lung cancer all resulted in restoration of chemo sensitivity. The results are highly consistent with the studies with ALDH1A1 inhibitor therapy being highly synergistic with chemotherapy and reversing chemotherapy resistance in vivo in primary human tumor explants. The present invention is not limited to a particular mechanism. Indeed, an understanding of the mechanism is not necessary to practice the present invention. Nonetheless, the results suggest synergy with chemotherapy may be more than just reduction in chemotherapy cellular metabolism. Based upon the single agent activity of the compounds to eliminate cells with cancer stemlike activity synergy is likely also in part due to the elimination of these inherently chemo resistant cells.

Disulfiram is a potent LDH inhibitor however it has broad ALDH isoform targeting capacity, with primary activity targeting ALDH2. While disulfiram demonstrates some modest ability to deplete CD133+ cells, it did not eliminate tumor initiation capacity alone or in combination with chemotherapy. The present invention is not limited to a particular mechanism. Indeed, an understanding of the mechanism is not necessary to practice the present invention. Nonetheless, it is contemplated that ?UM673 demonstrates superiority to disulfiram due to specific enzyme targeting. Drugs such as disulfiram and daidizin, with broad ALDH targeting activity can lead to the induction of expression of ALDH isoforms. As such this may overcome the drug. In contrast with UM 673, ALDH isoform induction was not observed.

Many anticancer therapies work via the induction of apoptosis also known as programmed cell death. However, cancer cells and cancer stem cells have evolved numerous mechanisms to escape the induction of apoptosis. The induction of program cell necrosis may be a means to overcome cancer cell resistance to apoptosis. In fact, cells which cannot apoptosis may undergo program cell necrosis as a 'backup' mechanism to undergo cell death. As such it is been proposed that the induction of program cell necrosis could be a very potent means to enhance cancer therapy. The data described herein indicate that UM 673 is inducing program cell necrosis of cancer cells.

In conclusion, the present example describes small molecules that selectively inhibit ALDH1A1. This compound selectively depletes cells expressing ovarian cancer stem cell markers. This compound reduces O-ring cancer stem cell functional activity in both cell lines and primary human ovarian cancer samples. This compound is highly synergistic chemotherapy and leads to regression of chemo refractory primary human tumor explants.

TABLE 1

|  | 673A IC$_{50}$ | 673B IC$_{50}$ | DEAB IC$_{50}$ | B13 IC$_{50}$ |
|---|---|---|---|---|
| ALDH1A1 (WT) | 216 ± 22 nM | 450 ± 35 nM | 519 ± 75 nM (2 min incub) | 110 ± 15 nM |
| ALDH1A1 (S121) | 230 ± 10 nM | 1240 ± 118 nM | 1490 ± 240 nM | >20 uM |
| ALDH1A2 | 211 ± 36 nM | 800 ± 147 nM | >20 μM | >20 μM |
| ALDH1A3 | 170 ± 28 nM (2 min incub) | 1340 ± 480 nM (2 min incub) | >20 μM | 400 nM |
| ALDH2 | 1680 ± 190 nM | >20 μM | >20 μM | >20 μM |
| ALDH3A1 | >20 μM | >20 μM | >20 μM | >20 μM |

TABLE 2

Impact of UM673 on the tumor initiation capacity of in vitro treated, PI-/Annexin-FACS isolated live cells.

| No. of cells injected | In Vitro Treatment Groups | | | |
|---|---|---|---|---|
|  | Control | Cisplatin | UM673 | Cisplatin + UM673 |
| 200 | ND | 1/4 | 2/4 | 0/4 |
| 1000 | ND | 4/4 | 4/4 | 1/4 |
| 5000 | 4/4 | 8/8 | 4/5 | 6/10 |

ND: Not Done.

All publications and patents mentioned in the above specification are herein incorporated by reference. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of treating ovarian cancer, comprising: administering a compound having the structure

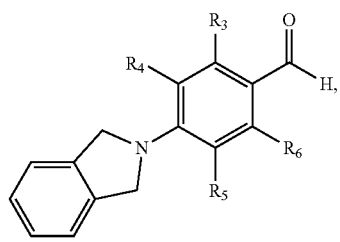

wherein R3-R6 are independently selected from the group consisting of a halogen, H, an alkyl, a cycloalkyl, an aryl, an alkenyl, a cycloalkyl, alkynl, and a substituted version of the aforementioned groups to a subject diagnosed with ovarian cancer under conditions such that said compound kills or inhibits the growth of said ovarian cancer.

2. The method of claim 1, wherein said administering prevents recurrence or metastasis of said ovarian cancer.

3. The method of claim 1, wherein said compound has the structure:

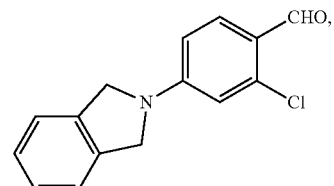

wherein R3 is selected from the group consisting of a halogen, H, an alkyl, a cycloalkyl, an aryl, an alkenyl, a cycloalkyl, alkynl, and a substituted version of the aforementioned groups.

4. The method of claim 1, wherein said compound is selected from the group consisting of,

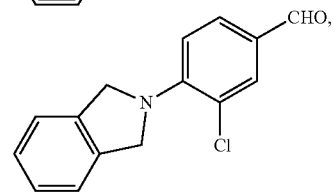

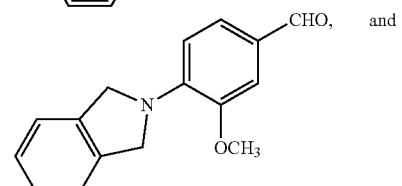

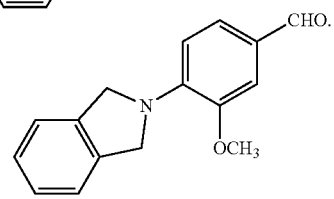

5. The method of claim 1, wherein said compound inhibits an ALDH enzyme.

6. The method of claim 5, wherein said ALDH enzyme is ALDH1A1.

7. The method of claim 1, wherein said method further comprises administering or co-administering a known chemotherapeutic agent.

8. The method of claim 7, wherein said known chemotherapeutic agent is selected from the group consisting of a cancer stem cell inhibitor, a platinum containing compound, and a taxane.

9. The method of claim 1, wherein said ovarian cancer is chemotherapy resistant ovarian cancer.

10. A method of treating ovarian cancer, comprising:
administering a compound selected from the group consisting of

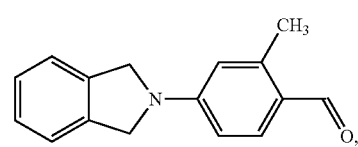

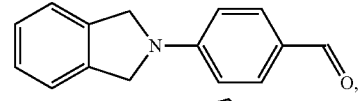

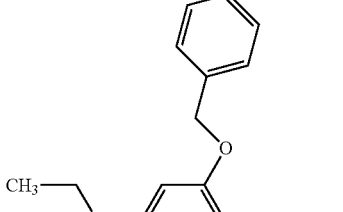

and

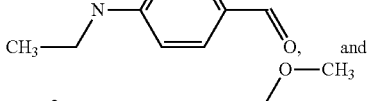

to a subject diagnosed with ovarian cancer under conditions such that said compound kills or inhibits the growth of said ovarian cancer.

11. The method of claim 10, wherein said compound is

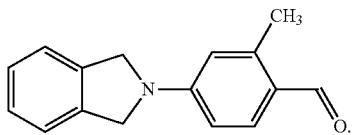 [SMILES: Cc1cc(N2Cc3ccccc3C2)ccc1C=O]

12. The method of claim 10, wherein said compound is

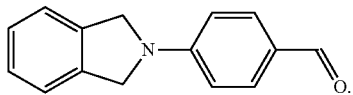

13. The method of claim 10, wherein said compound is

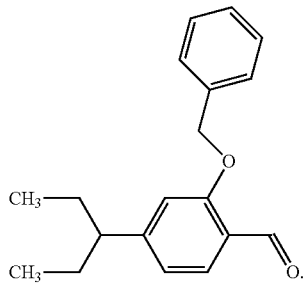 [SMILES: CCC(CC)c1ccc(C=O)c(OCc2ccccc2)c1]

14. The method of claim 10, wherein said compound is

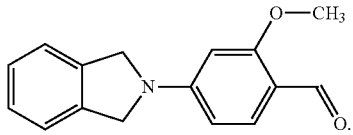 [SMILES: COc1cc(N2Cc3ccccc3C2)ccc1C=O]

* * * * *